(12) United States Patent
Park et al.

(10) Patent No.: US 12,214,004 B2
(45) Date of Patent: Feb. 4, 2025

(54) STRAINS HAVING EFFECTS OF PREVENTING OR TREATING CANCERS

(71) Applicant: Genome And Company, Gyeonggi-do (KR)

(72) Inventors: Hansoo Park, Seoul (KR); Shinyoung Park, Gyeonggi-do (KR); Eun Ju Lee, Gyeonggi-do (KR); Jae-Sung Yeon, Gyeonggi-do (KR); Hye Hee Jeon, Gyeonggi-do (KR); Wonduck Kim, Gyeonggi-do (KR); Joo-Yeon Chung, Gyeonggi-do (KR); Areum Jeong, Gyeonggi-do (KR); Youn Kyung Houh, Gyeonggi-do (KR); Jinyoung Sohn, Gyeonggi-do (KR); Yun Yeon Kim, Gyeonggi-do (KR); Sang Gyun Kim, Gyeonggi-do (KR); Suro Lee, Gyeonggi-do (KR)

(73) Assignee: Genome And Company, Seongnam-Si (KR)

( * ) Notice: Subject to any disclaimer, the term of this patent is extended or adjusted under 35 U.S.C. 154(b) by 970 days.

(21) Appl. No.: 17/096,031

(22) Filed: Nov. 12, 2020

(65) Prior Publication Data
US 2021/0138003 A1 May 13, 2021

Related U.S. Application Data

(62) Division of application No. 17/054,433, filed as application No. PCT/KR2019/005518 on May 8, 2019.

(30) Foreign Application Priority Data

May 11, 2018 (KR) .................. 10-2018-0054195
Nov. 1, 2018 (KR) .................. 10-2018-0133030

(51) Int. Cl.
| | |
|---|---|
| A61K 35/745 | (2015.01) |
| A61K 31/282 | (2006.01) |
| A61K 31/337 | (2006.01) |
| A61K 31/475 | (2006.01) |
| A61K 31/513 | (2006.01) |

(Continued)

(52) U.S. Cl.
CPC .......... *A61K 35/745* (2013.01); *A61K 31/282* (2013.01); *A61K 31/337* (2013.01); *A61K 31/475* (2013.01); *A61K 31/513* (2013.01); *A61K 31/519* (2013.01); *A61K 31/675* (2013.01); *A61K 31/704* (2013.01); *A61K 31/7048* (2013.01); *A61K 31/7068* (2013.01); *A61K 33/243* (2019.01); *A61K 35/744* (2013.01); *A61K 39/3955* (2013.01); *A61K 45/06* (2013.01); *A61P 35/00* (2018.01); *C07K 16/2818* (2013.01); *C07K 16/2827* (2013.01); *C12N 1/205* (2021.05); *A61K 2039/505* (2013.01); *A61K 2039/545* (2013.01)

(58) Field of Classification Search
CPC .. A61K 35/745; A61K 31/282; A61K 31/337; A61K 31/475; A61K 31/513; A61K 31/519; A61K 31/675; A61K 31/704; A61K 31/7048; A61K 31/7068; A61K 33/243; A61K 35/744; A61K 39/3955; A61K 45/06; A61P 35/00
See application file for complete search history.

(56) References Cited

U.S. PATENT DOCUMENTS

| | | | |
|---|---|---|---|
| 2016/0199423 A1 | 7/2016 | McKenzie et al. | |
| 2017/0354697 A1* | 12/2017 | Schneider | .............. A61K 35/74 |

FOREIGN PATENT DOCUMENTS

| | | |
|---|---|---|
| CN | 107603921 A | 1/2018 |
| CN | 107629988 A | 1/2018 |

OTHER PUBLICATIONS

Raschke (Current Opinion in Structural Biology, 16: 152-159, 2006).*

(Continued)

*Primary Examiner* — Nelson B Moseley, II
(74) *Attorney, Agent, or Firm* — Servilla Whitney LLC

(57) ABSTRACT

The present invention relates to a novel *Bifidobacterium bifidum* MG731 strain and a composition for preventing or treating cancers, comprising the same. Specifically, the *Bifidobacterium bifidum* MG731 strain of the present invention has effects of inhibiting the proliferation of cancer cells, decreasing the mobility of cancer cells, inhibiting the neoangiogenesis, and increasing the anticancer immune response as well as reducing the expression of inflammatory factors, thereby having effects of preventing or treating cancers or inflammatory diseases. In addition, when used in combination with an anticancer chemotherapeutic agent or an anticancer immunotherapeutic agent, the *Bifidobacterium bifidum* MG731 strain of the present invention exhibits a better anticancer effect. In addition, the present invention relates to a novel *Lactococcus lactis* GEN3033 strain and a composition for preventing or treating cancers, comprising the same. Specifically, the *Lactococcus lactis* GEN3033 strain of the present invention exhibits effects of directly inhibiting the proliferation of cancer cells and enhancing immunity, thereby having effects of preventing or treating cancers. In particular, the strain has an excellent anticancer effect by secreting metabolites having an anticancer effect while being established in the gut. In addition, when used in combination with an anticancer chemotherapeutic agent or an anticancer immunotherapeutic agent, the *Lactococcus lactis* GEN3033 strain of the present invention exhibits a better anticancer effect.

17 Claims, 31 Drawing Sheets
Specification includes a Sequence Listing.

(51) Int. Cl.
  *A61K 31/519* (2006.01)
  *A61K 31/675* (2006.01)
  *A61K 31/704* (2006.01)
  *A61K 31/7048* (2006.01)
  *A61K 31/7068* (2006.01)
  *A61K 33/243* (2019.01)
  *A61K 35/744* (2015.01)
  *A61K 39/395* (2006.01)
  *A61K 45/06* (2006.01)
  *A61P 35/00* (2006.01)
  *C07K 16/28* (2006.01)
  *C12N 1/20* (2006.01)
  *A61K 39/00* (2006.01)

(56) References Cited

OTHER PUBLICATIONS

Han, Kyoung Jun, et al., "Anticancer and Anti-Inflammatory Activity of Probiotic Lactococcus lactis NK34", J. Microbiol. Biotechnol. (2015), 25(10), 1697-1701, http://dx.doi.org/10.4014/jmb.1503.03033.

Ku, Seockmo, et al., "Review on Bifidobacterium bifidum BGN4: Functionality and Nutraceutical Applications as a Probiotic Microorganism", Int. J. Mol. Sci. 2016, 17, 1544; doi:10.3390/ijms17091544.

Kurek, Krzysztof, et al., "Metabolism, Physiological Role, and Clinical Implications of Sphingolipids in Gastrointestinal Tract", Hindawi Publishing Corporation, BioMed Research International, vol. 2013, Article ID 908907, 10 pages, http://dx.doi.org/10.1155/2013/908907.

Li, Jun, et al., "Probiotics modulated gut microbiota suppresses hepatocellular carcinoma growth in mice", PNAS, 2016, 113 (9), E1306-E1315.

Sivan, Ayelet, et al., "Commensal Bifidobacterium promotes antitumor immunity and facilitates anti-PD-L1 efficacy", Science. Nov. 27, 2015; 350(6264): 1084-1089. doi:10.1126/science.aac4255.

\* cited by examiner

SEQUENCE LISTING

<160> NUMBER OF SEQ ID NOS: 2

<210> SEQ ID NO 1
<211> LENGTH: 1447
<212> TYPE: DNA
<213> ORGANISM: Artificial Sequence
<220> FEATURE:
<223> OTHER INFORMATION: 16s rRNA Sequence of MG731

<400> SEQUENCE: 1

| | | | | | | |
|---|---|---|---|---|---|---|
| agacgctggc | ggcgtgctta | acacatgcaa | gtcgaacggg | atccatcggg | ctttgcttgg | 60 |
| tggtgagagt | ggcgaacggg | tgagtaatgc | gtgaccgacc | tgccccatgc | tccggaatag | 120 |
| ctcctggaaa | cgggtggtaa | tgccggatgt | tccacatgat | cgcatgtgat | tgtgggaaag | 180 |
| attctatcgg | cgtgggatgg | ggtcgcgtcc | tatcagcttg | ttggtgaggt | aacggctcac | 240 |
| caaggcttcg | acgggtagcc | ggcctgagag | ggcgaccggc | cacattggga | ctgagatacg | 300 |
| gcccagactc | ctacgggagg | cagcagtggg | gaatattgca | caatgggcgc | aagcctgatg | 360 |
| cagcgacgcc | gcgtgaggga | tgaaggcctt | cgggttgtaa | acctcttttg | tttgggagca | 420 |
| agccttcggg | tgagtgtacc | tttcgaataa | gcgccggcta | actacgtgcc | agcagccgcg | 480 |
| gtaatacgta | gggcgcaagc | gttatccgga | tttattgggc | gtaaagggct | cgtaggcggc | 540 |
| tcgtcgcgtc | cggtgtgaaa | gtccatcgct | taacggtgga | tctgcgccgg | gtacgggcgg | 600 |
| gctggagtgc | ggtaggggag | actggaattc | ccggtgtaac | ggtggaatgt | gtagatatcg | 660 |
| ggaagaacac | cgatggcgaa | ggcaggtctc | tgggccgtca | ctgacgctga | ggagcgaaag | 720 |
| cgtggggagc | gaacaggatt | agataccctg | gtagtccacg | ccgtaaacgg | tggacgctgg | 780 |
| atgtggggca | cgttccacgt | gttccgtgtc | ggagctaacg | cgttaagcgt | cccgcctggg | 840 |
| gagtacggcc | gcaaggctaa | aactcaaaga | aattgacggg | ggcccgcaca | agcggcggag | 900 |
| catgcggatt | aattcgatgc | aacgcgaaga | accttacctg | gcttgacat | gttcccgacg | 960 |
| acgccagaga | tggcgtttcc | cttcggggcg | ggttcacagg | tggtgcatgg | tcgtcgtcag | 1020 |
| ctcgtgtcgt | gagatgttgg | gttaagtccc | gcaacgagcg | caaccctcgc | cccgtgttgc | 1080 |
| cagcacgtta | tggtgggaac | tcacggggga | ccgccggggt | taactcggag | gaaggtgggg | 1140 |
| atgacgtcag | atcatcatgc | cccttacgtc | cagggcttca | cgcatgctac | aatggccggt | 1200 |
| acagcgggat | gcgacatggc | gacatggagc | ggatccctga | aaaccggtct | cagttcggat | 1260 |
| cggagcctgc | aacccggctc | cgtgaaggcg | gagtcgctag | taatcgcgga | tcagcaacgc | 1320 |
| cgcggtgaat | gcgttcccgg | gccttgtaca | caccgcccgt | caagtcatga | aagtgggcag | 1380 |
| cacccgaagc | cggtggccta | accccttgtg | ggatggagcc | gtctaaggtg | aggctcgtga | 1440 |
| ttgggac | | | | | | 1447 |

<210> SEQ ID NO 2
<211> LENGTH: 1470
<212> TYPE: DNA
<213> ORGANISM: Artificial Sequence
<220> FEATURE:
<223> OTHER INFORMATION: 16s rRNA Sequence of GEN3033

<400> SEQUENCE: 2

| | | | | | | |
|---|---|---|---|---|---|---|
| gacgaacgct | ggcggcgtgc | ctaatacatg | caagttgagc | gctgaaggtt | ggtacttgta | 60 |
| ccgactggat | gagcagcgaa | cgggtgagta | acgcgtgggg | aatctgcctt | tgagcggggg | 120 |
| acaacatttg | gaaacgaatg | ctaataccgc | ataaaaactt | taaacacaag | ttttaagttt | 180 |
| gaaagatgca | attgcatcac | tcaaagatga | tcccgcgttg | tattagctag | ttggtgaggt | 240 |

```
aaaggctcac caaggcgatg atacatagcc gacctgagag ggtgatcggc cacattggga    300
ctgagacacg gcccaaactc ctacgggagg cagcagtagg gaatcttcgg caatggacga    360
aagtctgacc gagcaacgcc gcgtgagtga agaaggtttt cggatcgtaa aactctgttg    420
gtagagaaga acgttggtga gagtggaaag ctcatcaagt gacggtaact acccagaaag    480
ggacggctaa ctacgtgcca gcagccgcgg taatacgtag gtcccgagcg ttgtccggat    540
ttattgggcg taaagcgagc gcaggtggtt tattaagtct ggtgtaaaag gcagtggctc    600
aaccattgta tgcattggaa actggtagac ttgagtgcag gagaggagag tggaattcca    660
tgtgtagcgg tgaaatgcgt agatatatgg aggaacaccg gtggcgaaag cggctctctg    720
gcctgtaact gacactgagg ctcgaaagcg tggggagcaa acaggattag ataccctggt    780
agtccacgcc gtaaacgatg agtgctagat gtagggagct ataagttctc tgtatcgcag    840
ctaacgcaat aagcactccg cctggggagt acgaccgcaa ggttgaaact caaaggaatt    900
gacgggggcc cgcacaagcg gtggagcatg tggtttaatt cgaagcaacg cgaagaacct    960
taccaggtct tgacatactc gtgctattcc tagagatagg aagttccttc gggacacggg   1020
atacaggtgg tgcatggttg tcgtcagctc gtgtcgtgag atgttgggtt aagtcccgca   1080
acgagcgcaa cccctattgt tagttgccat cattaagttg ggcactctaa cgagactgcc   1140
ggtgataaac cggaggaagg tggggatgac gtcaaatcat catgccccct atgacctggg   1200
ctacacacgt gctacaatgg atggtacaac gagtcgcgag acagtgatgt ttagctaatc   1260
tcttaaaacc attctcagtt cggattgtag gctgcaactc gcctacatga agtcggaatc   1320
gctagtaatc gcggatcagc acgccgcggt gaatacgttc ccgggccttg tacacaccgc   1380
ccgtcacacc acgggagttg ggagtacccg aagtaggttg cctaaccgca aggagggcgc   1440
ttcctaaggt aagaccgatg actggggtga                                    1470
```

STRAINS HAVING EFFECTS OF PREVENTING OR TREATING CANCERS

CROSS-REFERENCE TO RELATED APPLICATIONS

This application is a divisional application of U.S. application Ser. No. 17/054,433, filed on Nov. 10, 2020, which is the National Stage entry of PCT/KR2019/005518, filed on May 8, 2019, which claims priority to Korean Application Ser. No. 10-2018-0054195, filed May 11, 2018, and Korean Application Ser. No. 10-2018-0133030, filed Nov. 1, 2018, the entire disclosures of which are hereby incorporated by reference herein.

CROSS-REFERENCE TO SEQUENCE LISTING

The Sequence Listing identified as "CNP0028-01DV_SeqList_ST25.txt" (4,461 bytes), created Jan. 27, 2021 is hereby incorporated by reference.

TECHNICAL FIELD

The present invention relates to a novel *Bifidobacterium bifidum* MG731 strain and *Lactococcus lactis* GEN3033 strain having an excellent effect of preventing or treating cancers.

Specifically, the novel *Bifidobacterium bifidum* MG731 strain of the present invention not only has an effect of inhibiting the proliferation of cancer cells, but also has effects of decreasing the mobility of cancer cells and regulating the expression of genes involved in neoangiogenesis, thereby having a much excellent effect compared to the existing *Bifidobacterium bifidum* strain. In addition, the *Bifidobacterium bifidum* MG731 strain of the present invention has anti-inflammatory, antioxidant, and immune enhancing effects.

In addition, the novel *Lactococcus lactis* GEN3033 strain of the present invention not only has an effect of inhibiting the proliferation of cancer cells themselves, but also enhances immune activity, thereby having a much excellent effect compared to the existing *Lactococcus lactis* strain. Specifically, the *Lactococcus lactis* GEN3033 strain of the present invention has an excellent anticancer effect by secreting metabolites having an anticancer efficacy while being established in the gut.

BACKGROUND ART

The intestine of human body has an important function of absorbing nutrients through digestion of food and excreting unnecessary substances from inside of the body into outside of the body through the symbiosis of various kinds of bacteria. In addition, changes in the environment caused by intestinal bacteria are directly related to intestinal immunity, which in turn affects the immunity in the body. As research on these microorganisms beneficial to intestinal health has been continued for many years, research results on the involvement of lactic acid bacteria in the intestinal function, immunity, and metabolic activity in the body have been actively published worldwide. Probiotics, which are referred to as living microorganisms, ameliorate the imbalance in the digestive organ, inhibit harmful bacteria, and reinforce the natural defense effect to function to improve the immune response in the body. In the meantime, studies on the function of probiotics for improving intestinal immune function have been conducted according to the taxonomic morphology of species and genus using *Lactobacillus, Lactococcus, Bifidobacterium* and the like.

Research on lactic acid bacteria began in the 1900s when Metchnikoff announced the effect of prolonging lifespan by lactic acid bacteria. In 1946, based on the facts that when *Streptococcus pyogenes* and *Serratia marcescen* were infused directly into the tumor in patients with osteosarcoma, some patients exhibited tumor therapeutic response, studies on anticancer treatment by lactic acid bacteria have been in full swing, and many preclinical and clinical studies are still actively being conducted.

In 2016, El-Nezami research team found that when L. rhamnosus GG, *E. coli* Nissle 1917 and heat-treated VSL#3 were mixed at a certain ratio and administered orally to a mouse allogeneic tumor model, they had an anticancer effect through inhibition of the neoangiogenesis process compared to cisplatin, an anticancer agent. In addition, it was demonstrated that the group administered with the anticancer agent showed body weight loss in mice due to the toxicity of the anticancer agent, while the group administered with the probiotics did not show body weight loss. Thus, it was demonstrated that probiotics can have a function as an anticancer therapeutic agent. However, the probiotics used in the above studies contain multiple types of complex microorganisms, and studies on function of each microorganism were insufficient.

Unlike normal cells, cancer has infinite cell proliferation capacity, and its proliferation rate is also fast, and is one of the terrifying diseases that form a tumor microenvironment using blood vessels, lymphatic vessel, and fibroblasts and the like surrounding cancer cells, thereby causing metastasis to other tissue and loss of function of normal cells and the like, and thus leading to death.

In order to treat such cancer, researchers around the world are conducting a number of studies on various topics such as intracellular signaling mechanisms and metastasis of cancer cells, side effects of drugs and the like, and new drugs are developed every year, and clinical trials are being conducted to expect therapeutic effects to many patients with cancer.

In addition to surgical removal of tumor tissue and radiation therapy, current anticancer agents used in the anticancer treatment are applied differently depending on each type of cancer. Since anticancer chemotherapeutic agents generally prescribed to patients with cancer do not target cancer cells, they have the effect of killing cancer cells, but they also affect normal cells to lead to side effects such as hair loss, diarrhea, fever, and immunity decline in patients. Thereafter, based on genetic research on cancer, a target anticancer agent that targets genetic variations occurring in each carcinoma has been developed, and the side effects caused by existing anticancer chemotherapeutic agents have been greatly ameliorated. However, in order to escape from the attack of the target anticancer drug, cancer cells that adapt very quickly to the environment cause anticancer agent resistance, and thus, there is a problem that the sustained cancer therapeutic effect by the target anticancer agent cannot be expected by 100%.

Recently, studies on anticancer agents and tumor microenvironment have been actively conducted, and anticancer immunotherapeutic agents have been developed in relation with several immune checkpoint inhibitors that regulate the patient's immunity while maintaining an anticancer effect, and are being used as therapeutic agents for patients. Among them, treatment for PD-1/PD-L1 is known to exhibit high therapeutic response to patients with skin cancer, lung cancer, and the like. These anticancer immunotherapeutic agents have a function of inhibiting the proliferation of cancer cells and increasing the activity of immune cells by regulating the function of immune cells in the tumor microenvironment. However, anticancer immunotherapeutic agents also do not exhibit the same anticancer effect in all patients, and biomarkers for anticancer immunotherapeutic agents are not clearly identified, and anticancer agent resistance occurs due to JAK-STAT genetic variation, or autoimmune diseases may be caused due to the properties of antibody synthetics, and there are problems such as expensive treatment costs.

Based on these research results, the present inventors have conducted studies on microorganisms that can substantially ameliorate the therapeutic effect in patients with cancer, and have found that both a *Bifidobacterium bifidum* MG731 strain and a *Lactococcus lactis* GEN3033 strain exhibit an excellent effect of inhibiting the proliferation of cancer cells and the like. Based on the above, the present inventors completed the present invention.

DETAILED DESCRIPTION OF THE INVENTION

Technical Problem

The present invention is to utilize probiotics or an extract thereof exhibiting anticancer and anti-inflammatory effects for the development of novel anticancer agents, therapeutic agents for inflammatory diseases or therapeutic agents for immune diseases or the like.

Therefore, an object of the present invention is to provide a *Bifidobacterium bifidum* MG731 strain having an excellent effect of preventing or treating cancers.

Another object of the present invention is to provide a pharmaceutical composition for preventing or treating cancers, comprising a *Bifidobacterium bifidum* MG731 strain.

In addition, an object of the present invention is to provide a food composition or an animal feed composition for preventing or ameliorating cancers, comprising a *Bifidobacterium bifidum* MG731 strain.

In addition, an object of the present invention is to provide a novel *Lactococcus lactis* GEN3033 strain having an excellent effect of preventing or treating cancers.

Another object of the present invention is to provide a pharmaceutical composition for preventing or treating cancers, comprising a *Lactococcus lactis* GEN3033 strain.

In addition, an object of the present invention is to provide a food composition or an animal feed composition for preventing or ameliorating cancers, comprising a *Lactococcus lactis* GEN3033 strain.

Solution to Problem

In order to achieve the above objects, the present invention provides a novel *Bifidobacterium bifidum* MG731 strain. The strain was deposited with the Korean Collection for Type Cultures, the Korea Research Institute of Bioscience and Biotechnology, under accession number KCTC13452BP on Jan. 4, 2018.

In addition, the present invention provides a pharmaceutical composition for preventing or treating cancers, comprising a *Bifidobacterium bifidum* MG731 strain. Specifically, the *Bifidobacterium bifidum* MG731 strain may refer to those that include the strain itself, a culture of the strain, or a cytoplasmic fraction obtained by crushing the strain.

The present invention provides a method for preventing or treating cancers in a subject in need thereof, comprising administering an effective amount of a *Bifidobacterium bifidum* MG731 strain to the above subject. As used herein, the term "subject" includes a human and a non-human animal. Non-human animals include all vertebrates, for example mammals and non-mammals, such as non-human primates, sheep, dog, cow, horse and the like. In addition, the present invention provides the use of the *Bifidobacterium bifidum* MG731 strain for preventing or treating cancers.

In particular, the *Bifidobacterium bifidum* MG731 strain of the present invention is characterized by exhibiting all anticancer, anti-inflammatory, antioxidant, and immune enhancing effects.

In the present invention, the cancer may be melanoma, squamous cell carcinoma, breast cancer, head and neck cancer, thyroid cancer, soft tissue sarcoma, osteosarcoma, testis cancer, prostate cancer, ovarian cancer, bladder cancer, skin cancer, brain cancer, angiosarcoma, mast cell tumor, leukemia, lymphoma, liver cancer, lung cancer, pancreatic cancer, gastric cancer, kidney cancer, colorectal cancer, hematopoietic tumor, neuroblastoma, epidermal carcinoma or a metastatic cancer thereof, but is not limited thereto. Preferably, in the present invention, the cancer may be lung cancer, colorectal cancer, gastric cancer, breast cancer, or liver cancer.

In the present invention, an inflammatory disease may be osteoarthritis, rheumatoid arthritis, gout, ankylosing spondylitis, tendonitis, aponeurositis, rheumatoid fever, lupus, fibromyalgia, psoriatic arthritis, asthma, atopy, Crohn's disease, or ulcerative colitis, but is not limited thereto.

The *Bifidobacterium bifidum* MG731 strain of the present invention may exhibit an anticancer effect by inhibiting the proliferation of cancer cells and decreasing the mobility of cancer cells. In addition, the *Bifidobacterium bifidum* MG731 strain of the present invention may exhibit an anticancer effect by inhibiting the expression of VEGF (vascular endothelial growth factor), Ang1 (Angiopoietin1), and Ang2 (Angiopoietin2), which are angiogenic factors.

In addition, the *Bifidobacterium bifidum* MG731 strain of the present invention may exhibit an anti-inflammatory or anticancer effect by inhibiting the expression of TNF-α. TNF-α is a cytokine secreted by immune cells during chronic or acute inflammatory responses such as infection in the human body, trauma, sepsis, and rheumatoid arthritis, and when the concentration of TNF-α increases, lipid and sugar metabolic processes in the cell are damaged. TNF-α is known as a cytokine that induces cell necrosis. However, the research results have been reported that when continuous stimulation of TNF-α is transmitted to cells, tumorigenic genes are generated due to the influence on intracellular metabolism, and abnormal proliferation of cells occurs, thereby promoting the induction of cancer.

The present invention relates to a pharmaceutical composition for preventing or treating cancers, characterized in that the pharmaceutical composition comprises a *Bifidobacterium bifidum* MG731 strain, and an anticancer chemotherapeutic agent or an anticancer immunotherapeutic agent. In addition, the present invention provides a method for preventing or treating cancers in a subject in need thereof, comprising administering an effective amount of a *Bifidobacterium bifidum* MG731 strain in combination with an anticancer chemotherapeutic agent or an anticancer immunotherapeutic agent to the above subject.

The anticancer chemotherapeutic agent may be oxaliplatin, pemetrexed, cisplatin, gemcitabine, carboplatin, fluorouracil (5-FU), cyclophosphamide, paclitaxel, vincristine, etoposide, doxorubicin, but is not limited thereto.

In addition, the anticancer immunotherapeutic agent may be anti-PD1, anti-PDL1, anti-CTLA, anti-Tim3, anti-LAG3 having an immune checkpoint inhibitory function, but is not limited thereto.

In the present invention, a *Bifidobacterium bifidum* MG731 strain; and an anticancer chemotherapeutic agent or an anticancer immunotherapeutic agent may be administered sequentially or simultaneously to a patient in need thereof.

In addition, the present invention relates to a food composition or an animal feed composition for preventing or ameliorating cancers, comprising a *Bifidobacterium bifidum* MG731 strain.

The food composition may be a health functional food, a dairy product, a fermented product, or a food additive, but is not limited thereto.

The present invention provides a novel *Lactococcus lactis* GEN3033 strain. The *Lactococcus lactis* GEN3033 strain was deposited with the Korean Collection for Type Cultures, the Korea Research Institute of Bioscience and Biotechnology, under accession number KCTC13684BP on Oct. 25, 2018.

In addition, the present invention provides a pharmaceutical composition for preventing or treating cancers, comprising a *Lactococcus lactis* GEN3033 strain. Specifically, the *Lactococcus lactis* GEN3033 strain may include the strain itself, a culture of the strain, or a cytoplasmic fraction obtained by crushing the strain.

The present invention provides a method for preventing or treating cancers in a subject in need thereof, comprising administering an effective amount of a *Lactococcus lactis* GEN3033 strain to the above subject. In addition, the present invention provides the use of the *Lactococcus lactis* GEN3033 strain for preventing or treating cancers.

In particular, the *Lactococcus lactis* GEN3033 strain of the present invention is characterized by exhibiting both anticancer effect and immune enhancing effect.

The cancer may be melanoma, squamous cell carcinoma, breast cancer, head and neck cancer, thyroid cancer, soft tissue sarcoma, osteosarcoma, testis cancer, prostate cancer, ovarian cancer, bladder cancer, skin cancer, brain cancer, angiosarcoma, mast cell tumor, leukemia, lymphoma, liver cancer, lung cancer, pancreatic cancer, gastric cancer, kidney cancer, colorectal cancer, hematopoietic tumor, neuroblastoma, epidermal carcinoma, or a metastatic cancer thereof, but is not limited thereto.

The *Lactococcus lactis* GEN3033 strain of the present invention may exhibit an anticancer effect by directly inhibiting the proliferation of cancer cells and activating immune cells. In addition, the *Lactococcus lactis* GEN3033 strain of the present invention may exhibit an anticancer effect by regulating metabolites according to the establishment in the gut.

Specifically, the *Lactococcus lactis* GEN3033 strain of the present invention may increase ganglioside GM3 (monosialodihexosylganglioside). Ganglioside GM3 is a compound having a structure of formula I below, which is [(2S,4S,5R)-2-{[(2S,3R,4S,5S,6R)-2-{[(2R,3S,4R,5R,6R)-6-{[(2S,3R)-2-docosanamido-3-hydroxyoctadecyl]oxy}-4,5-dihydroxy-2-(hydroxymethyl)oxan-3-yl]oxy}-3,5-dihydroxy-6-(hydroxymethyl)oxan-4-yl]oxy}-5-acetamido-4-hydroxy-6-[(1R,2R)-1,2,3-trihydroxypropyl]oxane-2-carboxylic acid].

[Formula I]

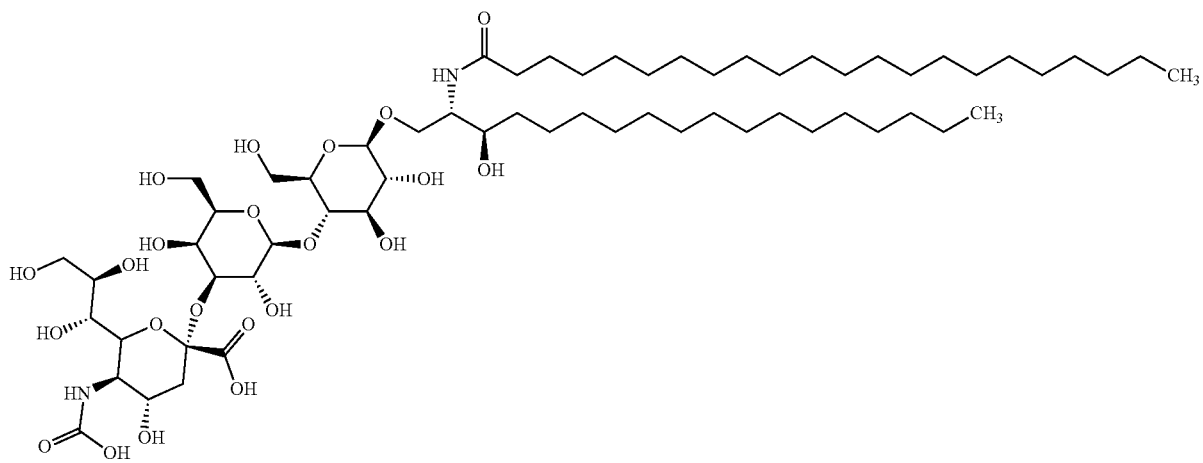

Ganglioside GM3, one of the glycosphingolipids, is a component of cell membrane, and is known to inhibit VEGF (vascular endothelial growth factor), thereby preventing angiogenesis and to regulate the arachidonic acid cascade of lymphocytes, thereby exhibiting an anticancer efficacy through the regulation of immune action. Moreover, ganglioside GM3 is known to further increase apoptosis in cancer cells when treated with cisplatin.

Therefore, the present invention relates to a pharmaceutical composition for preventing or treating cancers, characterized in that the *Lactococcus lactis* GEN3033 strain increases ganglioside GM3.

In addition, the *Lactococcus lactis* GEN3033 strain of the present invention may exhibit an anticancer effect and an immune enhancing effect by increasing the production of IFN-γ according to the activity of memory T cells, and increasing the expression of IL-15 and IL-7 that induce the activation of T cells.

Therefore, the present invention relates to a pharmaceutical composition for preventing or treating cancers, characterized in that the *Lactococcus lactis* GEN3033 strain increases the production of IFN-γ.

In addition, the present invention relates to a pharmaceutical composition for preventing or treating cancers, characterized in that the *Lactococcus lactis* GEN3033 strain increases the expression of IL-15 or IL-7.

The present invention relates to a pharmaceutical composition for preventing or treating cancers, characterized in that the pharmaceutical composition comprises a *Lactococcus lactis* GEN3033 strain; and an anticancer chemotherapeutic agent or an anticancer immunotherapeutic agent. In addition, the present invention provides a method for preventing or treating cancers in a subject in need thereof, comprising administering an effective amount of a *Lactococcus lactis* GEN3033 strain in combination with an anticancer chemotherapeutic agent or an anticancer immunotherapeutic agent to the above subject.

The anticancer chemotherapeutic agent may be oxaliplatin, pemetrexed, cisplatin, gemcitabine, carboplatin, fluorouracil (5-FU), cyclophosphamide, paclitaxel, vincristine, etoposide, doxorubicin, and the like, but is not limited thereto.

In addition, the anticancer immunotherapeutic agent may be anti-PD1, anti-PDL1, anti-CTLA, anti-Tim3, anti-LAG3 anticancer immunotherapeutic agent having an immune checkpoint inhibitory function, but is not limited thereto.

In the present invention, a *Lactococcus lactis* GEN3033 strain; and an anticancer chemotherapeutic agent or an anticancer immunotherapeutic agent may be administered sequentially or simultaneously to a patient in need thereof.

In addition, the present invention relates to a food composition or an animal feed composition for preventing or ameliorating cancers, comprising a *Lactococcus lactis* GEN3033 strain.

The food composition may be a health functional food, a dairy product, a fermented product, or a food additive, but is not limited thereto.

Effect of the Invention

The novel *Bifidobacterium bifidum* MG731 strain of the present invention has an effect of inhibiting the proliferation on various cancer cell lines. In addition, the *Bifidobacterium bifidum* MG731 strain of the present invention has an effect of decreasing the mobility of cancer cells and inhibiting the neoangiogenesis, and thus, it has a much excellent effect compared to other *Bifidobacterium bifidum* that are conventionally known.

In addition, the *Bifidobacterium bifidum* MG731 strain of the present invention may be also used for inflammatory diseases or immune diseases by having anti-inflammatory, antioxidant, or immune enhancing effects.

In particular, the *Bifidobacterium bifidum* MG731 strain of the present invention not only exhibits an excellent anticancer effect when administered alone, but also has a more excellent anticancer effect when administered in combination with an anticancer chemotherapeutic agent or an anticancer immunotherapeutic agent compared to when administering them alone.

The novel *Lactococcus lactis* GEN3033 strain of the present invention not only has an effect of inhibiting the proliferation on various cancer cell lines, but also exhibits immune activity, and thus, it has a much excellent effect compared to the existing *Lactococcus lactis* strain.

In particular, the *Lactococcus lactis* GEN3033 strain of the present invention not only exhibits an excellent anticancer effect when administered alone, but also has a more excellent anticancer effect when administered in combination with an anticancer chemotherapeutic agent or an anticancer immunotherapeutic agent compared to when administering them alone.

MODE FOR WORKING THE INVENTION

Figure 1:
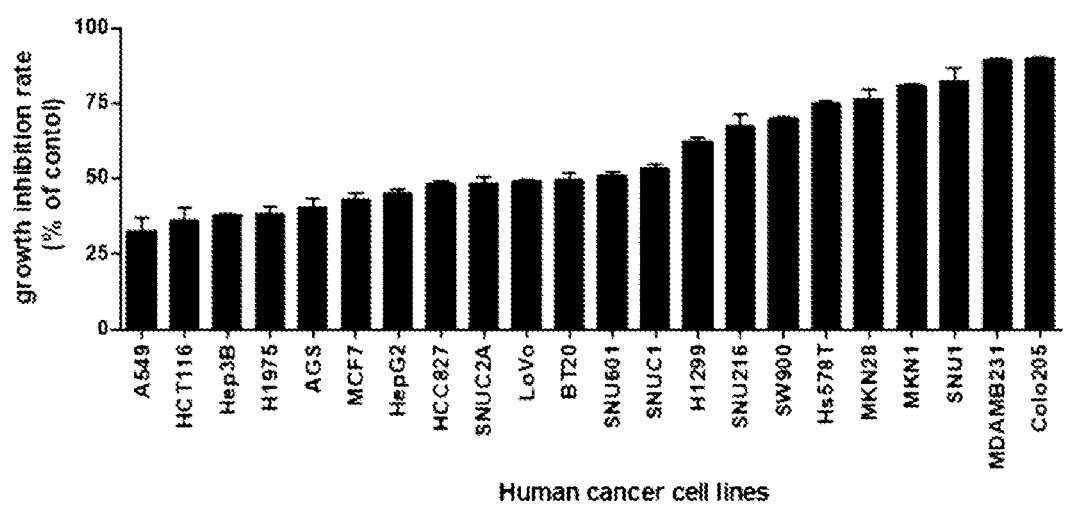
FIG. 1 is a graph showing the inhibition of cell proliferation according to MG731 treatment in human-derived cancer cell lines.

As a result of studying to discover probiotics having an excellent effect of treating or preventing cancers, the present inventors have confirmed that a novel *Bifidobacterium bifidum* MG731 strain and *Lactococcus lactis* GEN3033 strain have an excellent anticancer effect. Based on the above, the present inventors completed the present invention.

Surprisingly, the MG731 strain has an excellent effect of inhibiting the proliferation of cancer cells against various cancer cell lines such as lung cancer, colorectal cancer, gastric cancer, breast cancer, and liver cancer.

In addition, when the cancer cell line is treated with the MG731 strain, the mobility of cancer cells is remarkably reduced. Unlike normal cells, cancer cells are characterized by migrating upon proliferating even if the damage of cells occurs. In addition, the decrease in the mobility of cancer cells means that the possibility of cancer metastasis is lowered, so the MG731 strain has an effect of inhibiting cancer metastasis.

In addition, the MG731 strain can inhibit all the expression of VEGF (vascular endothelial growth factor), Ang1 (Angiopoietin1), and Ang2 (Angiopoietin2), which are major factors related to angiogenesis. Neoangiogenesis is one of the characteristics of cancer cells, and the inhibition of neoangiogenesis may inhibit the supply of nutrients to the cancer cells through blood vessels, thereby inhibiting the proliferation of cancer cells.

One of the distinctive aspects of inflammatory diseases is an increase in reactive oxygen species (ROS). A moderate concentration of reactive oxygen species exerts an effect through the regulation of the cellular signaling system, but in fact, exposure to a high concentration of reactive oxygen species for a long time causes non-specific damage to proteins, lipids, and nucleic acids. Reactive oxygen species play an important role in normal physiological processes such as protein phosphorylation, redox regulation of ion channels and transcription factors, and also have a major function in biosynthetic processes including production of thyroid hormone and crosslinking of extracellular matrix. In addition, it is well known that abnormal cell proliferation is induced since such reactive oxygen species have a high activity even in most cancer cells. Therefore, the MG731 strain of the present invention reduces reactive oxygen species, and thus, inhibits the proliferation of cancer cells, and has an effect of preventing the occurrence of various diseases.

In addition, the MG731 strain of the present invention induces more infiltration of cytotoxic T cells (CD8+ effector T cells) and NK cells (natural killer cells) into tumor tissues, which have the function of inhibiting the proliferation of tumor cells, and reduces the number of T regulatory cells that inhibit the function of cytotoxic T cells, thereby regulating the function of immune cells and exhibiting an excellent anticancer effect.

When various cancer cell lines are treated with the MG731 strain, and a known anticancer chemotherapeutic agent or anticancer immunotherapeutic agent, respectively, or in combination with the same, cancer cell lines treated with MG731 have an excellent effect of inhibiting the cell proliferation compared to cancer cell lines treated with an anticancer agent, and cancer cell lines treated with MG731 in combination with an anticancer agent have a better effect of inhibiting the cell proliferation compared to cancer cell lines treated with only MG731 or an anticancer agent, and thus, MG731 has an increased anticancer effect when administered in combination with an existing anticancer agent.

Therefore, the *Bifidobacterium bifidum* MG731 strain of the present invention may be utilized as an excellent anticancer agent by simultaneously exhibiting the effects of inhibiting the proliferation of cancer cells, decreasing the mobility of cancer cells, and inhibiting the neoangiogenesis, and may be administered in combination with an existing anticancer chemotherapeutic agent or anticancer immunotherapeutic agent.

The *Bifidobacterium bifidum* MG731 strain of the present invention may be administered simultaneously in one formulation with the anticancer chemotherapeutic agent or anticancer immunotherapeutic agent, or may be administered simultaneously or sequentially in separate formulations.

In addition, the MG731 strain may simultaneously prevent or treat inflammatory diseases and cancers by greatly reducing the expression of TNF-α induced by LPS, which is an inflammation-inducing factor.

The present invention provides a method for preventing or treating cancers, inflammatory diseases, immune diseases and the like by administering a *Bifidobacterium bifidum* MG731 strain into the body.

A composition comprising the *Bifidobacterium bifidum* MG731 strain of the present invention may be used in a pharmaceutical product, a health functional food, a dairy product, a fermented product, a food additive or an animal feed or the like.

In addition, the *Lactococcus lactis* GEN3033 strain of the present invention has an excellent effect of inhibiting the proliferation against various cancer cell lines.

When treated with the *Lactococcus lactis* GEN3033 strain of the present invention, the proliferation of cancer cells is directly reduced, and the production of IFN-γ is increased according to the activity of memory T cells, and the expression of IL-15 and IL-7, which induce the activation of T cells, is increased, and thus, anticancer and immune enhancing effects are exhibited.

In addition, the *Lactococcus lactis* GEN3033 strain of the present invention exhibits an anticancer effect by regulating metabolites according to the establishment in the gut. In particular, the *Lactococcus lactis* GEN3033 strain prevents neoangiogenesis by inhibiting VEGF, and increases ganglioside GM3 known to exhibit an anticancer efficacy through the regulation of immune action by regulating the arachidonic acid cascade of lymphocytes, and thus may exhibit an excellent anticancer effect. In addition, the *Lactococcus lactis* GEN3033 strain increases phosphatidylinositol (PI)

18:1 and 20:4, which regulates the immune response by activating macrophages. In addition, the administration of GEN3033 alone or an anticancer immunotherapeutic agent alone does not affect arachidonoyl thiophosphorylcholine and PC 16:0/22:6, which are known as markers exhibiting the damage of cell membrane and inflammatory response, but the combination administration of GEN3033 and an anticancer immunotherapeutic agent exhibits an anticancer efficacy by increasing arachidonoyl thiophosphorylcholine and PC 16:0/22:6.

When various cancer cell lines are treated with the GEN3033 strain, and a known anticancer chemotherapeutic agent or anticancer immunotherapeutic agent respectively or in combination, cancer cell lines treated with GEN3033 in combination with an anticancer agent have a more excellent effect of inhibiting the cell proliferation compared to cancer cell lines treated with only GEN3033 or an anticancer agent, and thus, GEN3033 has an increased anticancer effect when administered in combination with an existing anticancer agent.

Therefore, the *Lactococcus lactis* GEN3033 strain of the present invention may be utilized as an excellent anticancer agent by simultaneously exhibiting the effect of inhibiting the proliferation of cancer cells and the immune enhancing effect, and may be administered in combination with an existing anticancer chemotherapeutic agent or anticancer immunotherapeutic agent.

The *Lactococcus lactis* GEN3033 strain of the present invention may be administered simultaneously in one formulation with the anticancer chemotherapeutic agent or anticancer immunotherapeutic agent, or may be administered simultaneously or sequentially in separate formulations.

The present invention provides a method for preventing or treating cancers, inflammatory diseases, immune diseases and the like by administering a *Lactococcus lactis* GEN3033 strain into the body.

A composition comprising the *Lactococcus lactis* GEN3033 strain of the present invention may be used in a pharmaceutical product, a health functional food, a dairy product, a fermented product, a food additive or an animal feed or the like.

Hereinafter, the present invention is to be described in more detail through the following examples. It is intended that these examples illustrate the present invention in more detail, and the scope of the present invention is not limited to these examples.

Example 1

Isolation and Culture of *Bifidobacterium bifidum* MG731

The MG731 strain was isolated from the feces of healthy infants using a selective medium for *Bifidobacterium* spp.

The collected fecal sample was diluted serially 10-fold in 0.85% NaCl, plated on TOS-propionate agar (Merck KGaA, Darmstadt, Germany) added with 50 mg/L lithium mupirocin, and anaerobically cultured at a temperature of 37° C. for 48 hours, and then strains having different colony morphology were selected. The selected strains were subcultured in a BL broth, and then freeze stored at −80° C. in a BL broth containing 20% glycerol.

The nucleotide sequence of the rRNA for the obtained strain was analyzed and represented by SEQ ID NO: 1. As a result of identifying the strain, it was confirmed that MG731 was *Bifidobacterium bifidum*. The MG731 strain was deposited with the Korean Collection for Type Cultures, the Korea Research Institute of Bioscience and Biotechnology, under accession number KCTC13452BP on Jan. 4, 2018.

*Bifidobacterium bifidum* MG731 to be used in this experiment was inoculated into a MRS broth (Difco, USA) medium and cultured under an anaerobic condition at 37° C., and the culture was terminated when the proliferation of lactic acid bacteria reached OD=1. After the culture was completed, the cells were recovered from the culture through centrifugation, and the recovered cells were washed with PBS, and then suspended in PBS, and the cells were ground by ultrasonication method. The gound cells were centrifuged to obtain a supernatant and filtered through a 0.42 μm filter to prepare an extract of *Bifidobacterium bifidum* MG731.

Example 2

Effect of *Bifidobacterium bifidum* MG731 Strain on Inhibiting Tumor Proliferation In order to confirm whether *Bifidobacterium bifidum* MG731 exhibits an anticancer efficacy in various cancer cell lines, the MTT assay was performed using human-derived cancer cell lines.

Cancer cell lines used in the MTT assay include lung cancer (A549, H1975, HCC827, H1299, SW900), colorectal cancer (HCT116, LoVo, SNU-C2A, SNU-C1, Colo205), gastric cancer (SNU216, AGS, MKN-28, MKN-1, SNU-601, SNU-1), breast cancer (Hs578T, BT20, MDA-MB-231, MCF7), liver cancer (HepG2, Hep3B), and a total of 5 carcinomas were used in the experiment.

The cancer cell line was dispensed into a 96 well plate so as to be 1 to $5 \times 10^3$ cells/well, and after 24 hours, the a sample of lactic acid bacteria was added to 1% (1% =12.147 μg, the concentration of the extract was measured through BCA analysis), and after culturing for 72 hours, each well was treated with a reagent of MTT (3-(4,5-dimethylthiazol-2-yl)-2,5-diphenyltetrazolium bromide thiazolyl blue) reagent and reacted for 2 hours.

Then, in response to the mitochondria of living cells, the yellow MTT went through a process of turning purple. Thereafter, all the culture solution containing MTT was removed, and 100 μL of DMSO was added to each well, and the concentration of purple was measured at 540 nm absorbance using a Microplate reader apparatus, and the experimental results for human-derived cancer cell lines are shown in FIG. 1.

Example 3

Effect of *Bifidobacterium bifidum* MG731 Strain on Decreasing Mobility of Cancer Cells Unlike normal cells, cancer cells are characterized by migrating upon proliferating even if the damage of cells occurs. Thus, in order to confirm whether the mobility of cancer cells was decreased by the MG731 strain, a Wound healing assay was performed. A549 ($5 \times 10^5$ cells) and HCT116 ($6 \times 10^5$ cells) strains were attached to a 6 well plate, and when the cells became to be 90 to 95% proliferated, the cells were damaged at a constant interval using a tip. The cells were treated with PBS or the MG731 strain for 24 hours, and the presence or absence of the mobility of cells was observed under a microscope, and the results are shown in FIG. 2.

Figure 2A:
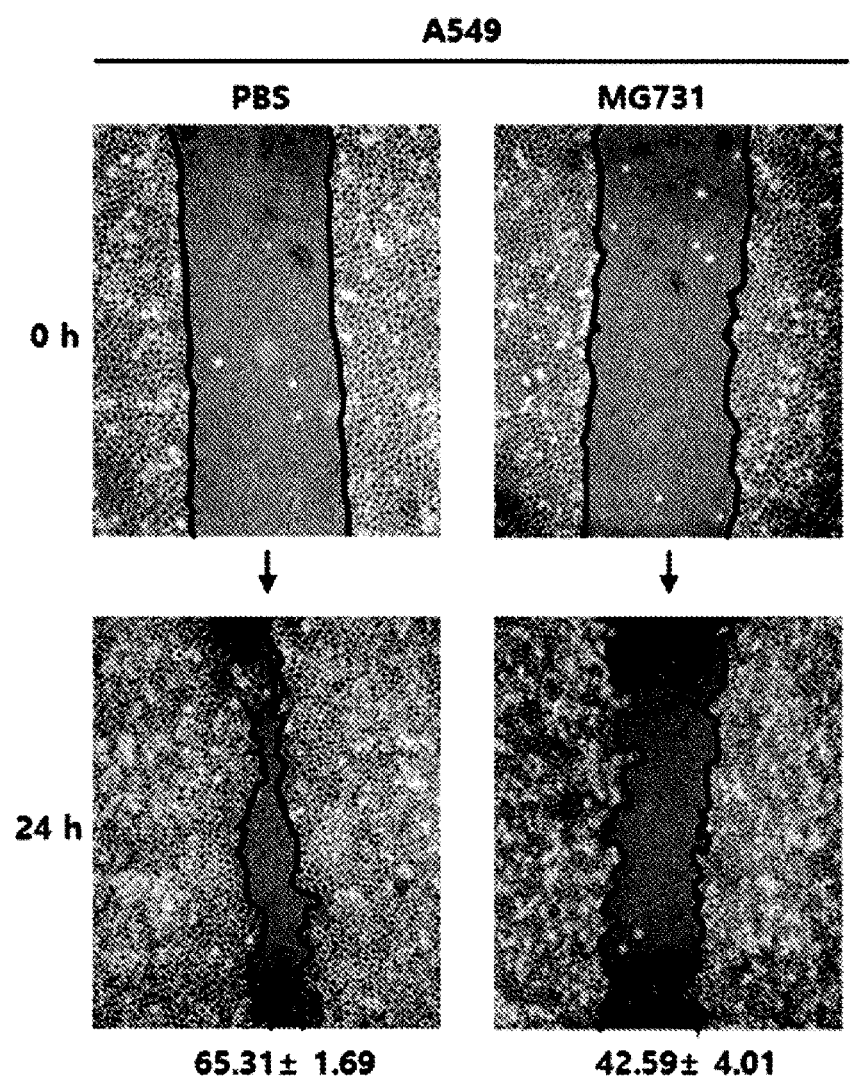
FIGS. 2a and 2b are results showing the decrease in the mobility of cancer cell lines by MG731.
Figure 2B:
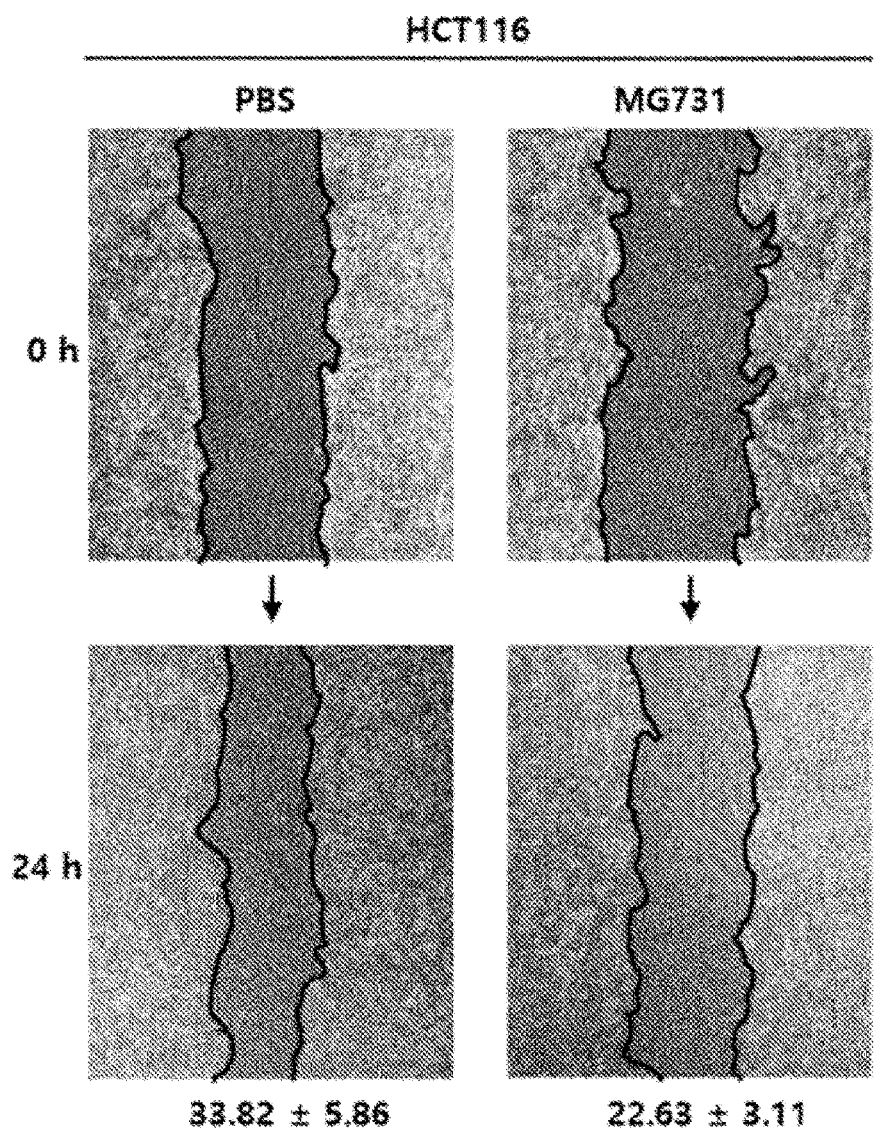

As shown in FIG. 2, when the cell status of the A549 (FIG. 2a) and HCT116 (FIG. 2b) cell lines at Hour 0 in which cells were damaged was set to the basis, after 24 hours, A549 had the mobility of cancer cells of 65.31±1.69%, and HCT116 had the mobility of cancer cells of 33.82±5.86%, indicating that the mobility of cancer cells was actively exhibited, whereas it was confirmed that A549 and HCT116 treated with MG731 had the mobility of cells of 42.59±4.01% and 22.63±3.11%, respectively, indicating that the mobility of cells was decreased.

As a result, it can be seen that the MG731 strain inhibits cancer metastasis and has an excellent anticancer effect.

Example 4

Effect of *Bifidobacterium bifidum* MG731 Strain on Inhibiting Neoangiogenesis

In order to confirm whether the MG731 strain inhibits the neoangiogenesis process, which is one of the characteristics of cancer cells, a test for the expression of neoangiogenesis related factors was performed as follows.

The HCT116 cell line was treated with MG731 for 24 hours, and then RNA was obtained, and cDNA was synthesized. Using this, the expression of VEGF, an angiogenic factor, was confirmed through general PCR, and the expression of Ang1 and Ang2 was confirmed through real-time PCR. The results are shown in FIGS. 3 and 4, respectively.

Figure 3:
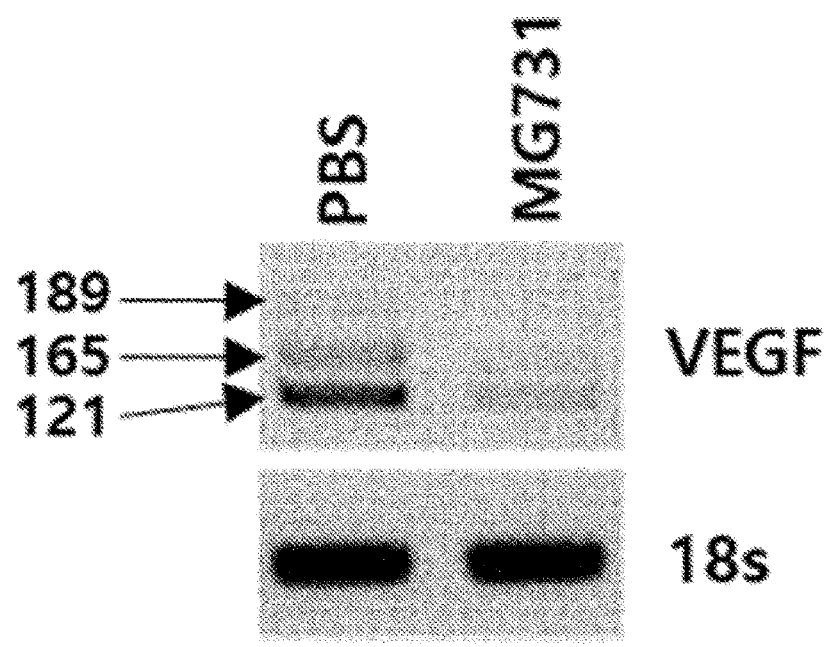
FIG. 3 shows that MG731 inhibited the expression of VEGF, a factor related to neoangiogenesis.

As shown in FIG. 3, it was confirmed that the expression of 121 isoform and 165 isoform of VEGF was remarkably reduced in the group treated with MG731 compared to the control group.

Figure 4A:
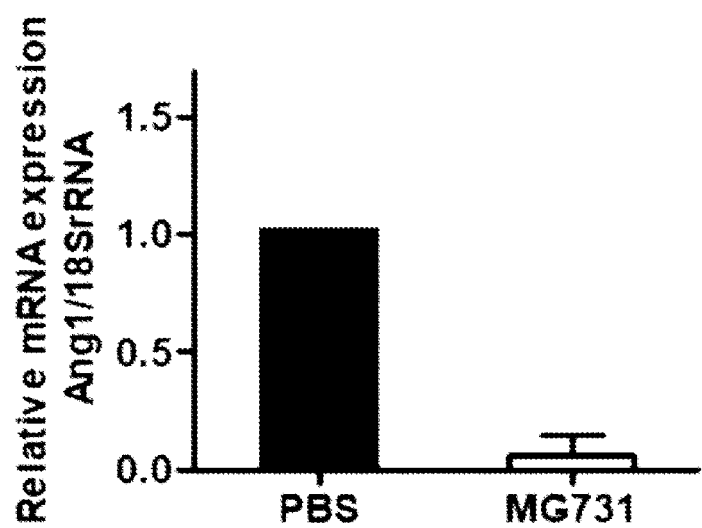
FIGS. 4a and 4b are results confirming the efficacy of MG731 inhibiting the expression of Ang1 and Ang2, which are factors related to neoangiogenesis other than VEGF.
Figure 4B:
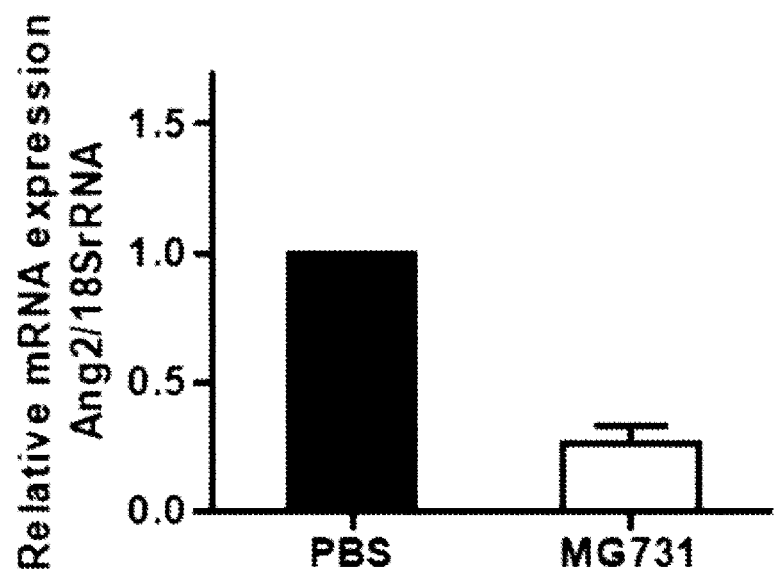

In addition, as shown in FIG. 4, it was confirmed that when the expression of Ang1 (FIGS. 4*a*) and Ang2 (FIG. 4*b*), factors involved in the neoangiogenesis, in addition to VEGF was compared, the expression rate was remarkably reduced by at least 70% when comparing the expression of Ang1 and Ang2 in the group treated with MG731 with the control group.

As a result, it can be seen that MG731 has an excellent effect on inhibiting the abnormal proliferation of cancer cells by inhibiting the neoangiogenesis and thus inhibiting the supply of nutrients to the cancer cells through blood vessels.

Example 5

Anti-Inflammatory Effect of *Bifidobacterium bifidum* MG731 Strain

In order to confirm the anti-inflammatory effect of the MG731 strain, the RAW264.7 cells, which are mouse macrophages, were treated with the MG731 strain for 18 hours, and then treated with 100 ng/ml of LPS, an inflammation-inducing factor, for 6 hours to obtain RNA.

Figure 5:
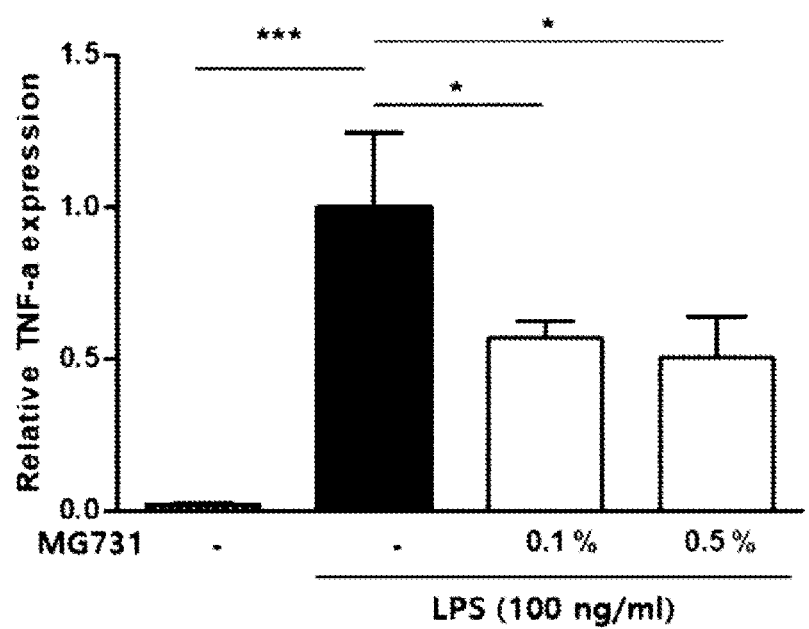
FIG. 5 shows that MG731 inhibited the expression of TNF-α among factors that induce an inflammatory response by LPS.

The cDNA was synthesized with 1 µg of the RNA, and through this, the presence or absence of the expression of TNF-α, which is known as an inflammatory factor, was confirmed through real-time PCR, and the results are shown in FIG. 5.

As shown in FIG. 5, when the degree of increase in the expression of TNF-α by LPS was set to a relative index of 1, it was confirmed that the degree of increase in the expression of TNF-α in the group treated with MG731 was 0.5 or less. Since TNF-α is also known as a cancer-inducing factor, it can be seen that MG731 has anti-inflammatory and anti-cancer functions at the same time from the remarkably reduced expression of TNF-α by MG731.

Example 6

Antioxidant Activity Effect of *Bifidobacterium bifidum* MG731 Strain

Figure 6:
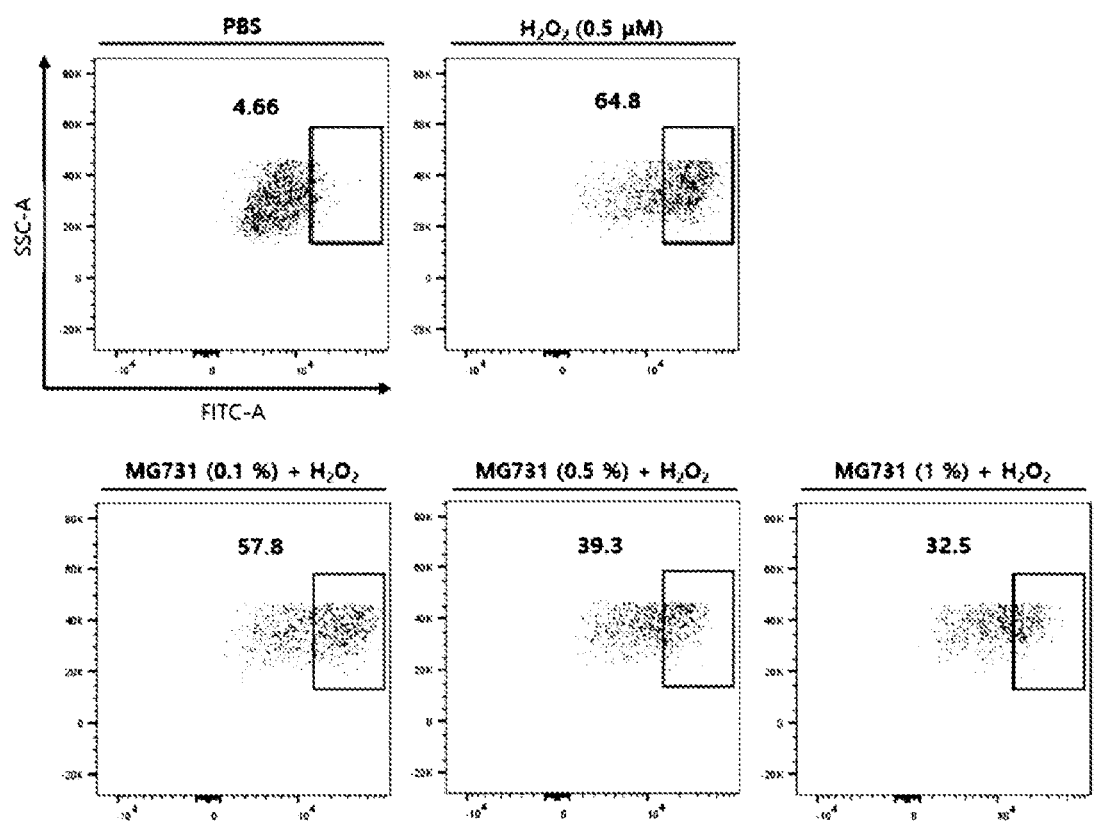
FIG. 6 shows the reduction of reactive oxygen species according to the treatment by concentration of MG731.

In order to confirm the antioxidant activity of MG731, the A549 cancer cell line was treated with MG731 for 24 hours and then treated with 0.5 µM $H_2O_2$ for 4 hours, and the amount of reactive oxygen in the cell was measured with FACs apparatus through DCFDA fluorescent dye, and the results are shown in FIG. 6.

As shown in FIG. 6, it can be seen that the group treated with only PBS showed the amount of reactive oxygen of 4.66%, and the group treated with only $H_2O_2$ showed an increase in the amount of reactive oxygen of 64.8%. On the other hand, in the groups treated with 0.1, 0.5 and 1% of MG731, respectively, the amount of reactive oxygen was reduced to 57.8%, 39.3% and 32.5%. Therefore, it was confirmed that MG731 exhibited an effect of reducing the amount of reactive oxygen, and when the concentration of MG731 was increased, the effect of inhibiting reactive oxygen was also increased.

As a result, through the above experimental results, it can be seen that MG731 has an antioxidant effect. That is, in normal cells, it may play a role in protecting cell damage caused by reactive oxygen, and in cancer cells, it may play a role in controlling abnormal functions of mitochondria by reducing the abnormal concentration of reactive oxygen.

Example 7

Effect of Inhibiting the Proliferation of Cancer Cells According to Combination Treatment of *Bifidobacterium bifidum* MG731 Strain and Anticancer Agent (In Vitro Experiment)

In A549 and HCT116, an experiment on the inhibition of the proliferation of cancer cells according to combination treatment of MG731 and an anticancer agent was conducted. Using oxaliplatin or pemetrexed as an anticancer agent, the experiment was performed in the following manner.

The above two cancer cell lines were diluted and then dispensed into each well of a 6 well plate so as to be 1 to $2 \times 10^3$ and attached for 24 hours, and then treated with lactic acid bacteria and an anticancer agent for each well, and the medium was exchanged at an interval of 2 to 3 days, and the proliferation of cells was induced for 7 days.

The plate was treated with 4% formalin for 30 minutes to fix the cells to stop the cell proliferation, and then was washed with PBS twice, and stained with a crystal violet solution for 5 minutes, and then washed with distilled water to observe whether the cells were proliferated. The results are shown in FIG. 7.

Figure 7:
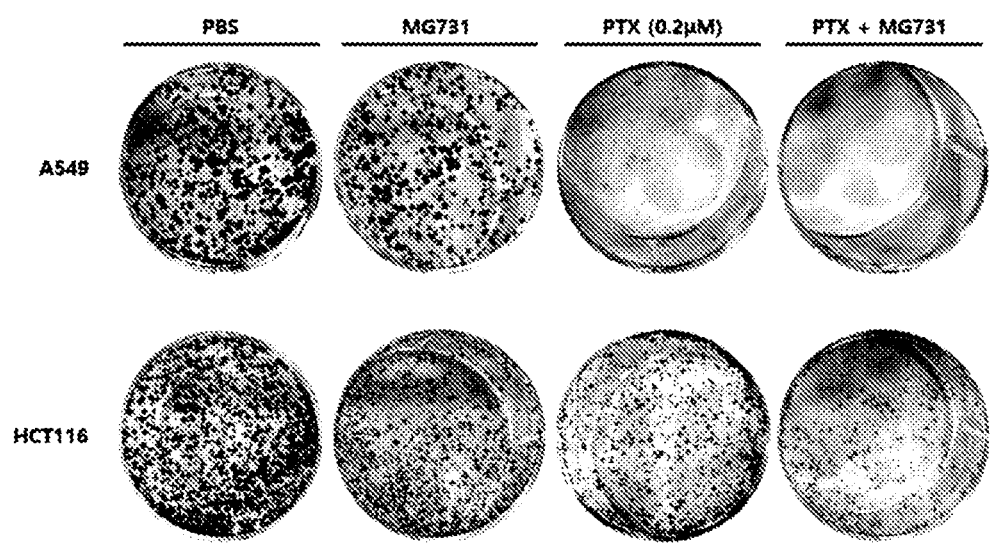
FIG. 7 is a result showing an effect of inhibiting the proliferation of cancer cells according to the combination treatment of an anticancer chemotherapeutic agent (oxaliplatin, pemetrexed) and MG731.

As shown in FIG. 7, it was found that the cancer cell line treated with the MG731 strain in combination with an anticancer agent exhibited a more excellent effect of inhibiting the cell proliferation compared to the cancer cell line treated with only MG731 or an anticancer agent.

Figure 8:
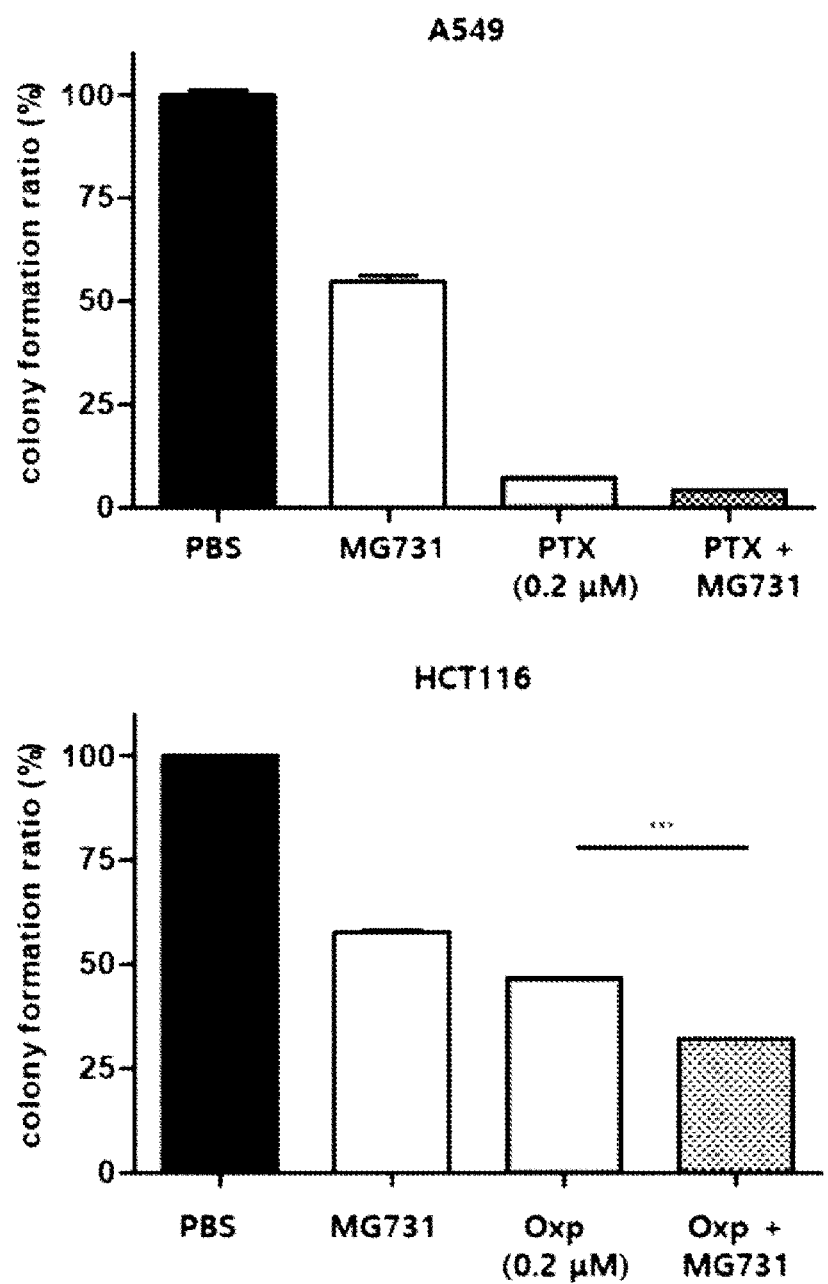
FIG. 8 is a result of destaining the stained cells in FIG. 7 and quantifying an effect of inhibiting the proliferation of cancer cells.

In addition, the concentration of the colony of stained cells was measured using a Microplate reader instrument by dissolving crystal violet in acetic acid, and the results are shown in FIG. 8. In FIG. 8, it was confirmed that the same effect as in FIG. 7 was exhibited.

Example 8

Antitumor Enhancing Effect According to Combination Administration of *Bifidobacterium bifidum* MG731 Strain and Anticancer Immunotherapeutic Agent (In Vitro Experiment)

PBMCs (peripheral blood mononuclear cells) were collected from the human blood using Ficoll, and then red blood cells were removed through RBC lysis buffer, and the number of living cells was counted, and the cells were cultured for 24 hours in a round bottom 96 well plate containing lactic acid bacteria ($6\times10^5$/50 ul/well) by adding PBMC $3 \times 10^4$ cells/50 µl to each well.

The colon cancer cell line HCT116 was mixed with 5 µM of CFSE (carboxyfluorescein succinimidyl ester) in RPMI medium without FBS, and reacted at 37° C. for 5 minutes, and then RPMI1640 medium containing FBS was added, and stored on ice for 10 minutes. After the supernatant was removed by centrifugation, the obtained cells were mixed with RPMI1640 containing 10% FBS, and then the number of cells was counted, and $3\times10^4$ cells/100 µl were added to each well of the above prepared 96 well plate.

Figure 9:
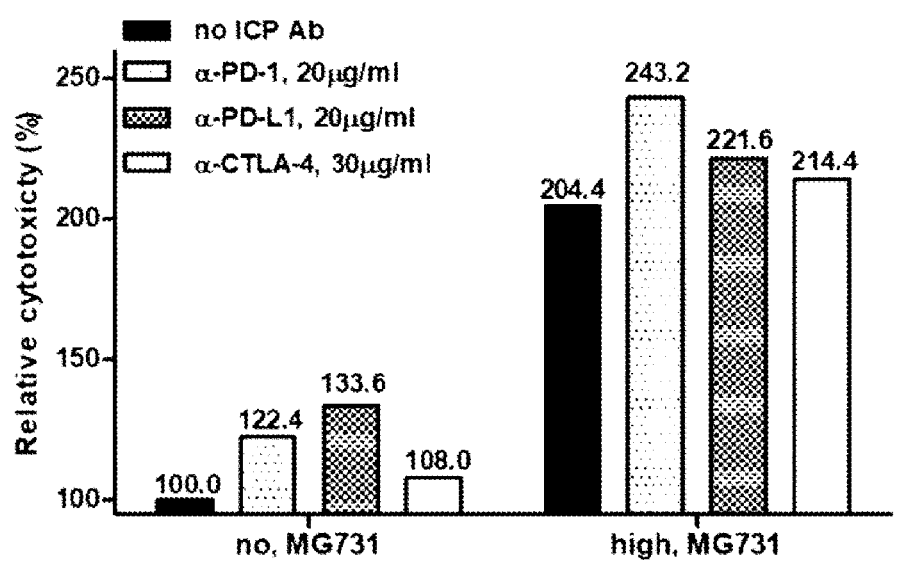
FIG. 9 shows the efficacy of cancer cell death by treatment of MG731 in combination with an anticancer immunotherapeutic agent (anti-PD1, anti-PD-L1, anti-CTLA4) using human blood and cancer cell lines.

Thereafter, each well to which cancer cells were added was treated with each antibody PD1 (Pembrolizumab, A2005, Selleckem), PD-L1 (Atezolizumab, A2004, Selleckem), CTLA-4 (Ipilimumab, A2001, Selleckem) within the concentration range of 20 to 30 ug/mL, and cultured for 24 hours, and then the cells were stained with 7-aminoactinomycin D (7-AAD; BD Pharmingen, San Diego, Calif., USA) to identify the cells lysed in a mixture of PBMC and cancer cell lines. Staining for CFSE and 7-AAD using FACSDiVa software (BD Biosciences) was measured to confirm the cell lysis ability of PBMC against cancer cell lines, and the results are shown in FIG. 9.

It was found that when the cancer cell death (cytotoxicity) caused by PBMC was set to 100%, the cancer cell death (cytotoxicity) caused by MG731 alone was 204.4% increase, and the cancer cell death caused by anti-PD1, an anticancer immunotherapeutic agent used in clinical practice, was 122.4%, and the cancer cell death caused by anti-PD-L1 was 133.6%, and the cancer cell death caused by antiCTLA-4 was 108%. On the other hand, it was confirmed that when treated with the anticancer immunotherapeutic agent in combination with MG731, the cancer cell death caused by anti-PD1 was 243.2%, and the cancer cell death caused by anti-PD-L1 was 221.6%, and the cancer cell death caused by antiCTLA-4 was 214.4%.

As a result, it can be seen that compared to the effect on the cancer cell death when administered alone, the effect on the cancer cell death when administered in combination is much excellent.

Example 9

Inhibitory Effect on Tumor Proliferation According to Combination Administration of *Bifidobacterium bifidum* MG731 Strain and Anticancer Agent (In Vivo Experiment)

Prior to constructing a tumor model, a sample of lactic acid bacteria was administered to mice for 2 weeks to increase intestinal establishment and immunity, and then $2\times10^5$ MC38 cancer cells were injected subcutaneously in the vicinity of the right hip of 8 C57BL/6 mice per group to construct a tumor-induced model. Simultaneously with injection of tumor cells, a sample of lactic acid bacteria was orally administered to the animal model for 3 weeks (from Monday to Saturday). The sample of lactic acid bacteria to be administered was diluted in 200 µL of PBS so as to be $1\times10^9$ of CFU per head and then administered orally. Oxaliplatin (3 mg/kg, Sellekchem) or anti-PD1 (2 mg/kg, BioXCell) as an anticancer agent was intraperitoneally injected every Monday and Thursday after cancer induction.

Figure 10:
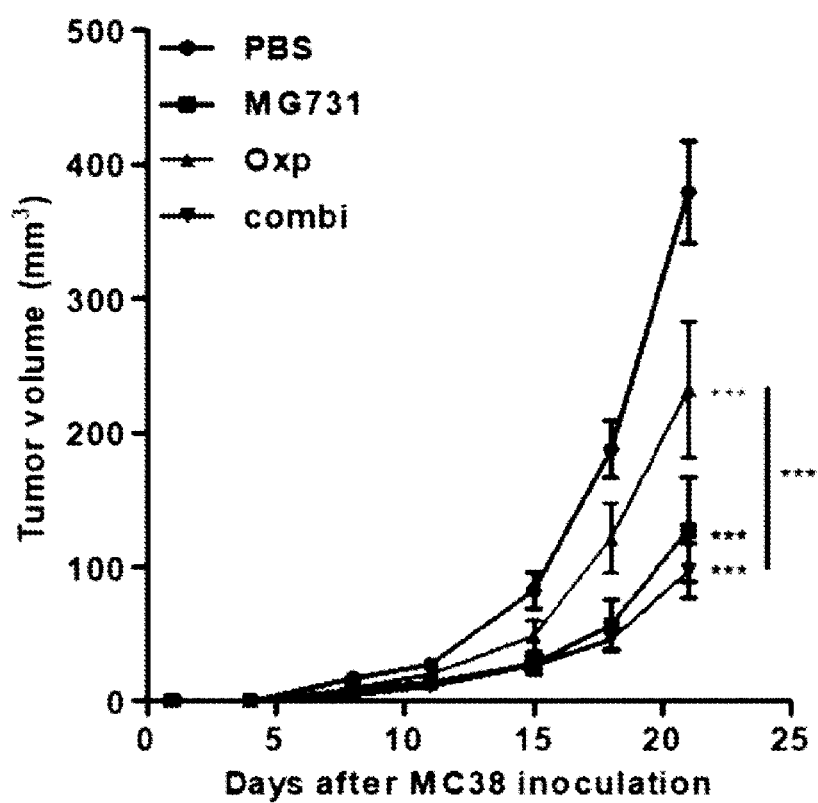
FIG. 10 shows an effect of inhibiting the tumor proliferation according to the combination administration of an anticancer chemotherapeutic agent (oxaliplatin) and MG731 using a mouse allograft model.
Figure 11:
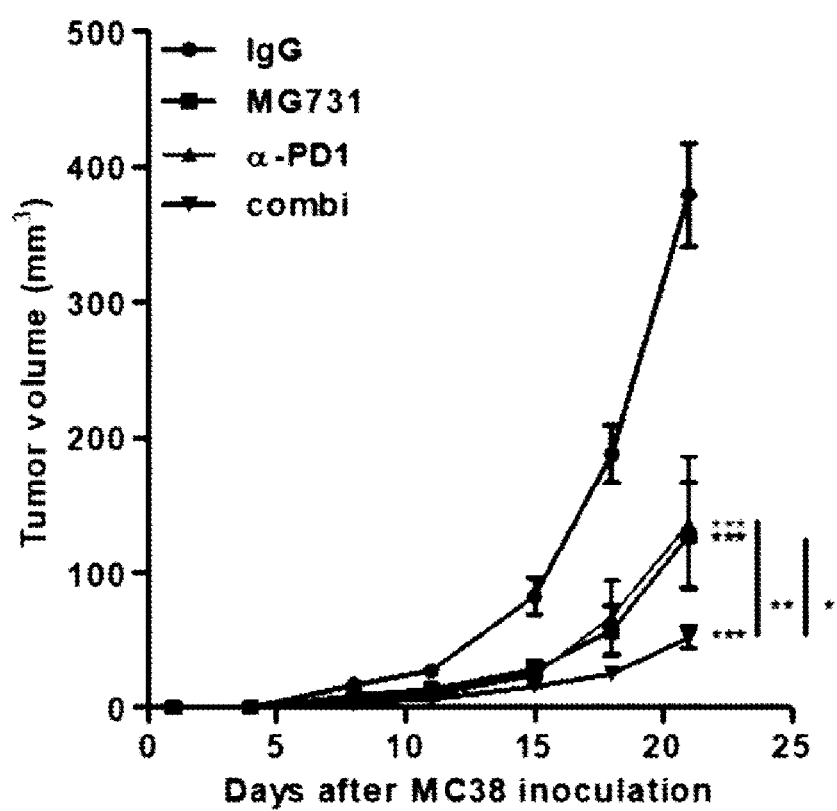
FIG. 11 shows an effect of inhibiting the tumor proliferation according to the combination administration of an anticancer immunotherapeutic agent (anti-PD1) and MG731 using a mouse allograft model.

The tumor inhibitory effect in the group treated with only lactic acid bacteria, the group treated with only oxaliplatin or anti-PD1, and the group treated with both was observed, and the results are shown in FIGS. 10 and 11.

As shown in FIGS. 10 and 11, when MG731 was administered alone, the tumor inhibitory effect was better than when oxaliplatin or anti-PD1 was administered alone, and it was confirmed that when MG731 was administered in combination with oxaliplatin or anti-PD1, the tumor inhibitory effect was more excellent.

Example 10

Effect of Enhancing Antitumor Immune Response According to Combination Administration of *Bifidobacterium bifidum* MG731 Strain and Anticancer Agent (In Vivo Experiment)

Based on the results of Example 9 above, in order to confirm the distribution of immune cells infiltrating into the tumor, the following animal experiment was conducted to perform FACs experiment.

In the same manner as in Example 9, a tumor-induced model was constructed, a sample of lactic acid bacteria and an anticancer agent were administered, and then the tumor and the spleen were separated, and the tissue was crushed and the immune cells were isolated to confirm the distribution of immune cells in the mice. The isolated immune cells were reacted using fluorescent antibodies corresponding to markers of immune cells according to each function, and then confirmed using FACs apparatus. The above experimental results are shown in FIGS. 12 and 13.

Figure 12:
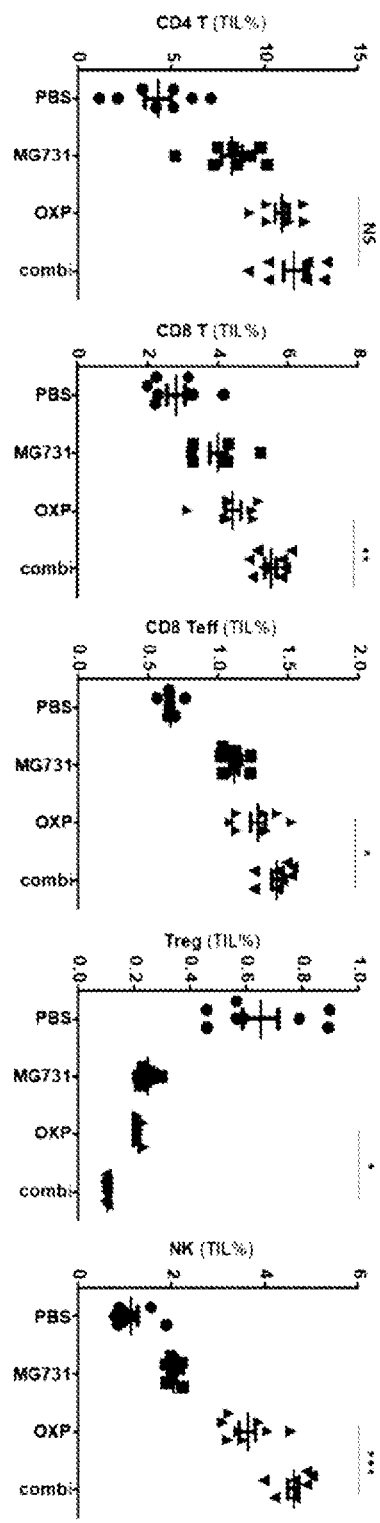
FIG. 12 is an analysis of the distribution of immune cells infiltrating into tumor tissues of a mouse allograft model according to the combination administration of an anticancer chemotherapeutic agent (oxaliplatin) and MG731.
Figure 13:
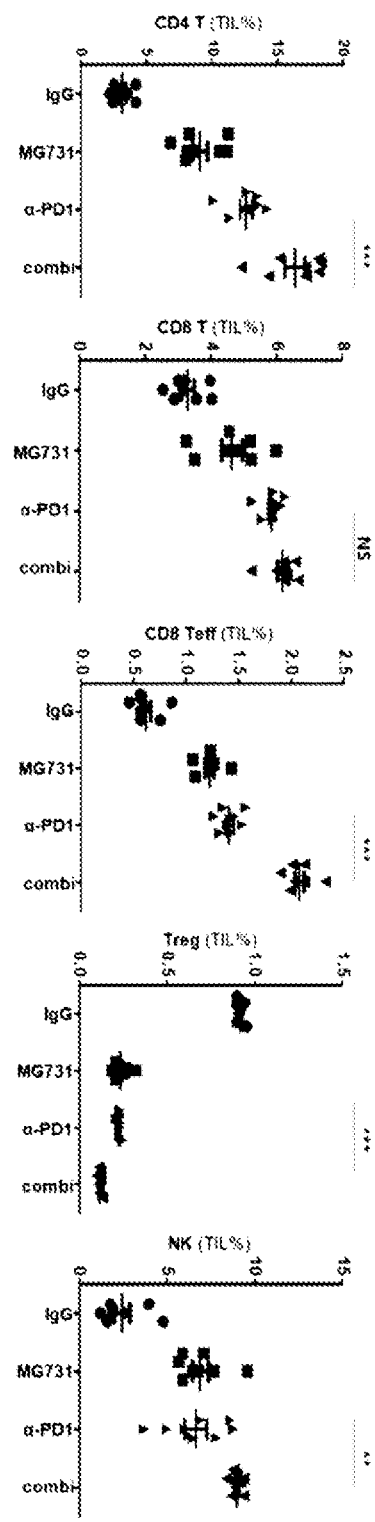
FIG. 13 is an analysis of the distribution of immune cells infiltrating into tumor tissues of a mouse allograft model according to the combination administration of an anticancer immunotherapeutic agent (anti-PD1) and MG731.

As shown in FIGS. 12 and 13, it was confirmed that in the group administered with MG731, the distribution of CD4 T cells, CD8 T cells, and CD8 effector T cells exhibiting an important function in anticancer immune response was increased by at least 1.5 to 2 times compared to the control group, IgG or PBS. In addition, it can be seen that the number of regulatory T cells that regulate the function of T cells was remarkably reduced.

In addition, in the group treated with MG731 in combination with an anticancer agent, the distribution of CD4 T cells, CD8 T cells, and CD8 effector T cells was significantly increased compared to the the group treated with an anticancer agent alone, and the number of regulatory T cells that regulate the function of T cells was significantly reduced. From the above results, it can be seen that when MG731 was administered in combination with an anticancer agent, the antitumor immune response was significantly increased compared to treatment with an anticancer agent alone.

From the above results, it can be seen that the regulation of immune cell function by MG731 also has an influence on the inhibition of tumor proliferation.

Example 11

Isolation and Identification of *Lactococcus lactis* GEN3033 Strain

In order to isolate the GEN3033 strain, feces were provided from a normal 41 yearold female. About 4 g of the collected fresh fecal sample was added to 80 ml of a PBS (phosphate buffered saline) solution, vortexed, and then re-suspended. The homogenized samples were serially diluted 10 times in the same solution, and among them, 200

μL of the samples diluted $10^{-5}$, $10^{-6}$, $10^{-7}$, $10^{-8}$ times were plated on a De Man Rogosa, Sharpe agar (MRS broth; Difco, USA) medium, which is a lactic acid bacteria selective medium, and were cultured for 48 hours at a temperature of 37° C. under an aerobic condition. A 16S rRNA gene (1.5 kb) amplified from each colony produced in a solid medium was obtained using a colony PCR method. After purification of the PCR sample, the nucleotide sequence of each 16S rRNA gene obtained through sequencing was applied to a NCBI blast program to search for related species.

Among them, the strain (1448/1448 bp, 100%) having a high similarity to *Lactococcus lactis* subsp. *lactis* strain 41MoQuesillo was designate as GEN3033. For pure isolation, colony restreaking in solid medium was performed 6 times, and then the reconfirmation of the nucleotide sequence of 16S rRNA gene was performed. The selected GEN3033 strain was freeze stored at −80° C. by adding 20% glycerol after liquid culture.

The nucleotide sequence of the rRNA for the obtained strain was analyzed and represented by SEQ ID NO: 2, and as a result of identifying the strain, GEN3033 was confirmed to be *Lactococcus lactis*. The GEN3033 strain was deposited with the Korean Collection for Type Cultures, the Korea Research Institute of Bioscience and Biotechnology, under accession number KCTC13684BP on Oct. 25, 2018.

1. Confirmation of Sugar Fermentation Properies

Sugar fermentation properties were investigated using the API CHL kit (BioMetrieux Co. France) for the GEN3033 strain, and the results are shown in Table 1 below.

TABLE 1

| No | Carbohydrates | GEN3033 |
|---|---|---|
| 0 | Control | − |
| 1 | Glycerol | − |
| 2 | Erythritol | − |
| 3 | D-arabinose | − |
| 4 | L- arabinose | − |
| 5 | Ribose | + |
| 6 | D-xylose | − |
| 7 | L-xylose | − |
| 8 | Adonitol | − |
| 9 | β-Methyl-xyloside | − |
| 10 | Galactose | + |
| 11 | Glucose | + |
| 12 | Fructose | + |
| 13 | Mannose | + |
| 14 | Sorbose | − |
| 15 | Rhamnose | − |
| 16 | Dulcitol | − |
| 17 | Inositol | − |
| 18 | Mannitol | − |
| 19 | Sorbitol | − |
| 20 | Methyl-D-mannoside | − |
| 21 | Methyl-D-glucoside | − |
| 22 | N-Acelyl-Glucosamine | + |
| 23 | Amygdalin | + |
| 24 | Arbutin | − |
| 25 | Esculin | + |
| 26 | Salicin | + |
| 27 | Cellobiose | + |
| 28 | Maltose | + |
| 29 | Lactose | − |
| 30 | Melibiose | − |
| 31 | Sucrose | + |
| 32 | Trehalose | + |
| 33 | Inulin | − |
| 34 | Melezitose | − |
| 35 | Raffinose | − |
| 36 | Starch | + |
| 37 | Glycogen | − |
| 38 | Xylitol | − |
| 39 | β Gentiobiose | + |

TABLE 1-continued

| No | Carbohydrates | GEN3033 |
|---|---|---|
| 40 | D-turanose | − |
| 41 | D-lyxose | − |
| 42 | D-tagatose | − |
| 43 | D-fucose | − |
| 44 | L-fucose | − |
| 45 | D-arabitol | − |
| 46 | L-arabitol | − |
| 47 | Gluconate | − |
| 48 | 2-Keto-Gluconate | − |
| 49 | 5-Keto Gluconate | − |

+: shows sugar fermentation effect;
−: does not show sugar fermentation effect

2. Confirmation of Enzyme Activity

In order to investigate the biochemical properties of the GEN3033 strain, the enzyme activity properties were investigated using API ZYM kit (BioMetrieux Co. France), and the results are shown in Table 2 below.

TABLE 2

| No. | Enzyme | Substrate | GEN3033* |
|---|---|---|---|
| 1 | Control | — | 0 |
| 2 | Alkaline phosphatase | 2-naphthyl phosphate | 1 |
| 3 | Esterase (C4) | 2-naphthyl butyrate | 0 |
| 4 | Esterase Lipase (C8) | 2-naphthyl caprylate | 0 |
| 5 | Lipase (C14) | 2-naphthyl myristate | 0 |
| 6 | Leucine arylamidase | L-leucyl-2-naphthylamide | 3 |
| 7 | Valine Arylamidase | L-valyl-2-naphthylamide | 0 |
| 8 | Cystine arylamidase | L-cystyl-2-naphthylamide | 0 |
| 9 | Trypsin | N-benzoyl-DL-arginine-2-naphthylamide | 0 |
| 10 | α-chymotrypsin | N-glutaryl-phenylalanine-2-naphthylamide5 | 0 |
| 11 | Acid phosphatase | 2-naphthyl phosphate (pH 5.4) | 5 |
| 12 | Naphthol-AS-BI-phosphogydrolase | Naphthol-AS-BI-phosphate | 2 |
| 13 | α-galactosidase | 6-Br-2-naphthyl-αD-galactopyranoside | 0 |
| 14 | β-galactosidase | 2-naphthyl-βD-galactopyranoside | 0 |
| 15 | β-glucuronidase | Naphthol-AS-BI-βD glucuronide | 0 |
| 16 | α-glucosidase | 2-naphthyl-αD-glucopyranoside | 0 |
| 17 | β-glucosidase | 6-Br-2-naphthyl-βD-glucopyranoside | 0 |
| 18 | N-acetyl-β-glucosaminidase | 1-naphthyl-N-acetyl-βD-glucosaminide | 0 |
| 19 | α-mannosidase | 6-Br-2-naphthyl-αD-mannopyranoside | 0 |
| 20 | α-flucosidase | 2-naphthyl-αL-fucopyranoside | 0 |

*0: 0 nanomol; 1: 5 nanomols; 2: 10 nanomols; 3: 20 nanomols; 4: 30 nanomols; 5: >40 nanomols Example 12

Immune Cell Activity Effect of *Lactococcus lactis* GEN3033 Strain

In order to confirm the immune activity of GEN3033, an experiment for change in the secretion of IFN-γ according to the activity of memory T cells was performed in the following manner.

PBMCs were isolated from human blood through Ficoll, red blood cells were removed with RBC lysis buffer, and monocytes were isolated using LS column and MACS buffer. Monocytes were added to a 96 well plate in which GEN3033 was dispensed so as to be $5\times10^3$ per well, and reacted for 2 hours so that GEN3033 could differentiate monocytes into macrophages.

During the reaction between monocytes and GEN3033, T cells expressing CD4 and CD8 were isolated from excess PBMC cells by using MACS buffer and LS column, and the isolated T cells were diluted in 100 μL of RPMI medium so as to be $5 \times 10^4$ cells, and dispensed into the wells containing monocytes and GEN3033, and then cultured for 48 hours to generate immune activity. After a certain period of time, the cell culture solution of each well was collected in a 1.5 ml tube, and only the supernatant was separated, and the degree of IFN-γ production was measured using an ELISA kit, and the results are shown in FIG. 14.

Figure 14:
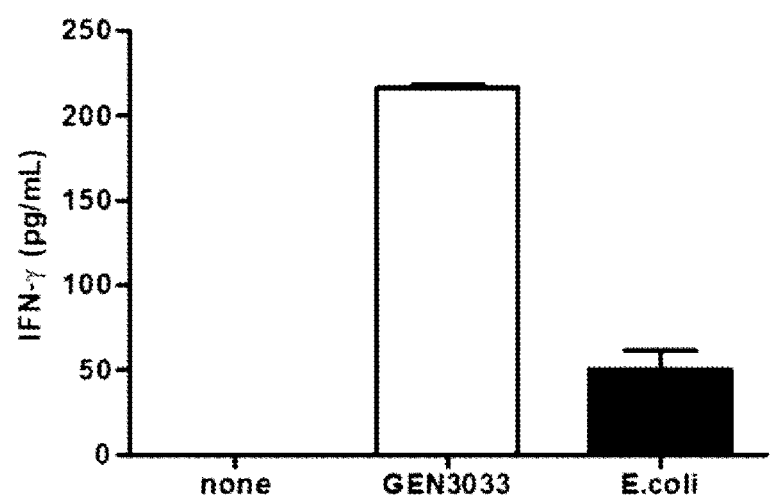
FIG. 14 is a result confirming an effect of increasing the production of IFN-γ as a biomarker of immune activity by the GEN3033 strain.

As shown in FIG. 14, it was confirmed that the wells containing only Monocytes and T cells did not produce IFN-γ, whereas the wells reacted with *E. coli* produced 50 pg/mL of IFN-γ, and the wells reacted with GEN3033 produced about 210 pg/mL of IFN-γ.

That is, it was confirmed that GEN3033 stimulated memory T cells by activating macrophages and induced the production of IFN-γ. As a result, it can be seen that GEN3033 remarkably increases the activity of memory T cells, resulting in an excellent immune activity.

Example 13

Antitumor Effect of *Lactococcus lactis* GEN3033 (In Vitro)

In order to confirm whether GEN3033 exhibits an anticancer efficacy in various cancer cell lines, CCK-8 assay was performed using 11 human-derived cancer cell lines.

The cancer cell line was dispensed into a 96 well plate so as to be 1 to $5 \times 10^3$ cells/well, and stabilized for 24 hours, and then a sample of crushed lactic acid bacteria was added to 1% (1%=4.965 μg, the concentration of the extract was measured through BCA analysis), and cultured for 72 hours, and the viability of the cancer cells identified using CCK-8 (DOJINDO, USA) is shown in Table 3 below.

TABLE 3

| Carcinoma | Name of cell line | Cell viability (% of control) |
| --- | --- | --- |
| Colorectal cancer | HCT116 | 20.688 ± 0.711 |
| Breast cancer | MDA-MB-231 | 28.919 ± 1.393 |
| Neuroblastoma | SH-SY5Y | 54.599 ± 5.182 |
| Brain tumor | T98G | 84.040 ± 2.904 |
| Gastric cancer | MKN28 | 25.262 ± 1.675 |
| Chronic myelogenous leukemia | K562 | 37.569 ± 5.139 |
| Pancreatic cancer | PANC-1 | 30.436 ± 3.045 |
| Lung cancer | A549 | 85.461 ± 3.033 |
| Osteosarcoma | U2-OS | 81.037 ± 4.412 |
| Liver cancer | HepG2 | 62.015 ± 5.618 |
| Epidermal carcinoma | A431 | 59.303 ± 2.929 |

As shown in Table 3 above, although the difference in cell viability by GEN3033 appears according to the properties of cancer cells, it was confirmed that the cell viability was reduced in all cell lines treated with GEN3033 compared to the untreated control group (cell viability of 100%).

Example 14

Effect of *Lactococcus lactis* GEN3033 Strain on Inhibiting Tumor Proliferation (In Vivo)

In the allogeneic mouse tumor model, tumors develop rapidly in a short period of time, and thus accurate efficacy cannot be confirmed due to tumor necrosis. Therefore, a sample of lactic acid bacteria was administered to mice for 2 weeks prior to the construction of the tumor model to induce the immune activity according to intestinal establishment of GEN3033.

Thereafter, tumor transplantation was performed by subcutaneously injecting $2 \times 10^5$ of MC38 cancer cell lines into the right leg of the mice, and then a sample of lactic acid bacteria was orally administered to the animal model for 3 weeks (from Monday to Saturday), and the sample of lactic acid bacteria to be administered was diluted in 200 μL of PBS so as to be $1 \times 10^9$ of CFU per head. Thereafter, the size of the tumor was measured in the mice, and the results are shown in FIG. 15.

Figure 15:
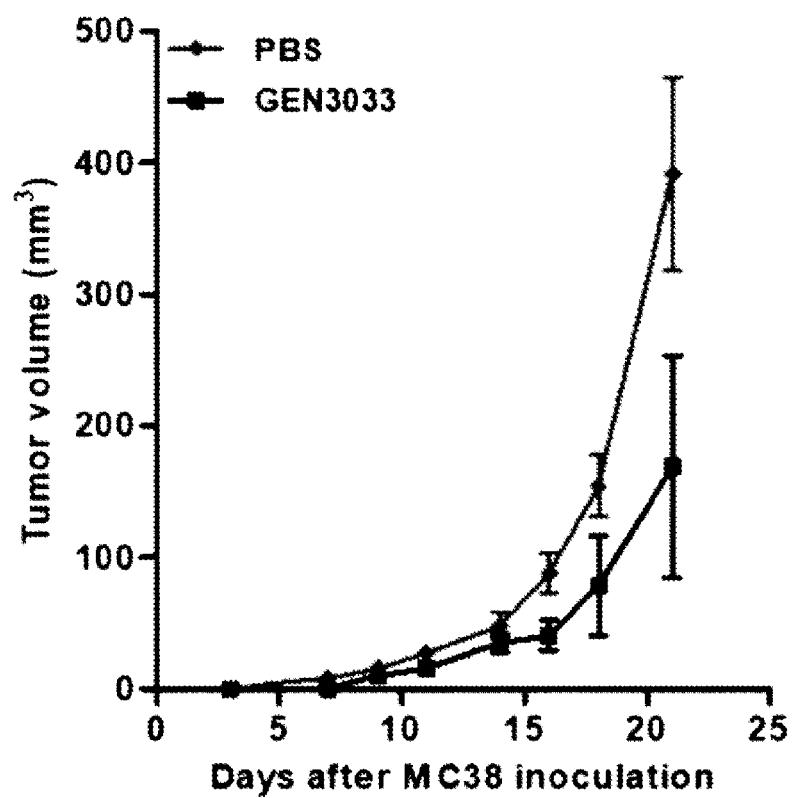
FIG. 15 is a result confirming an effect of inhibiting the tumor proliferation by administering the GEN3033 strain to a mouse tumor model.

As shown in FIG. 15, it was confirmed that the group administered with PBS, which is a negative control group, increased the tumor at a rapid rate over time, whereas the group administered with GEN3033 remarkably reduced the proliferation rate of the tumor compared to the control group. As a result, it can be seen that GEN3033 exhibits an antitumor therapeutic effect.

Example 15

Effect of *Lactococcus lactis* GEN3033 Strain on Expressing Immune Factor

Macrophages and dendritic cells are stimulated to secrete IL-15 and IL-7, which induce the activation of T cells. Therefore, the expression of IL-15 and IL-7, which induce the activation of T cells, from the large intestine and tumor tissues of the mice of Example 13 above was confirmed by qPCR. The results are shown in FIGS. 16 and 17.

Figure 16:
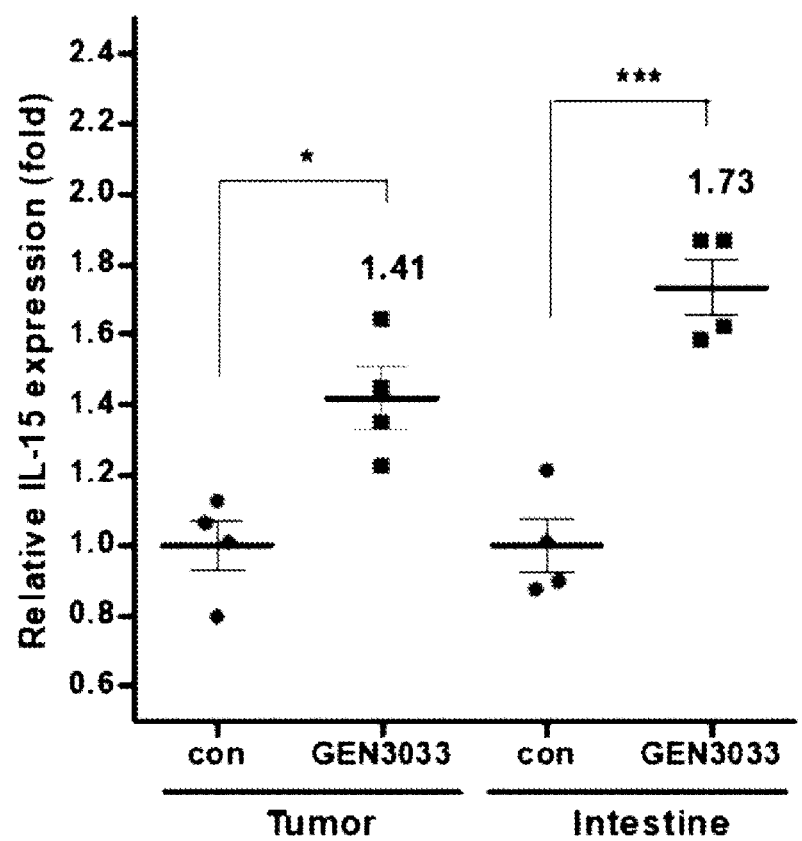
FIG. 16 is a result of measuring the expression of IL-15 in the large intestine and tumor tissue of a mouse tumor model to which the GEN3033 strain was administered.
Figure 17:
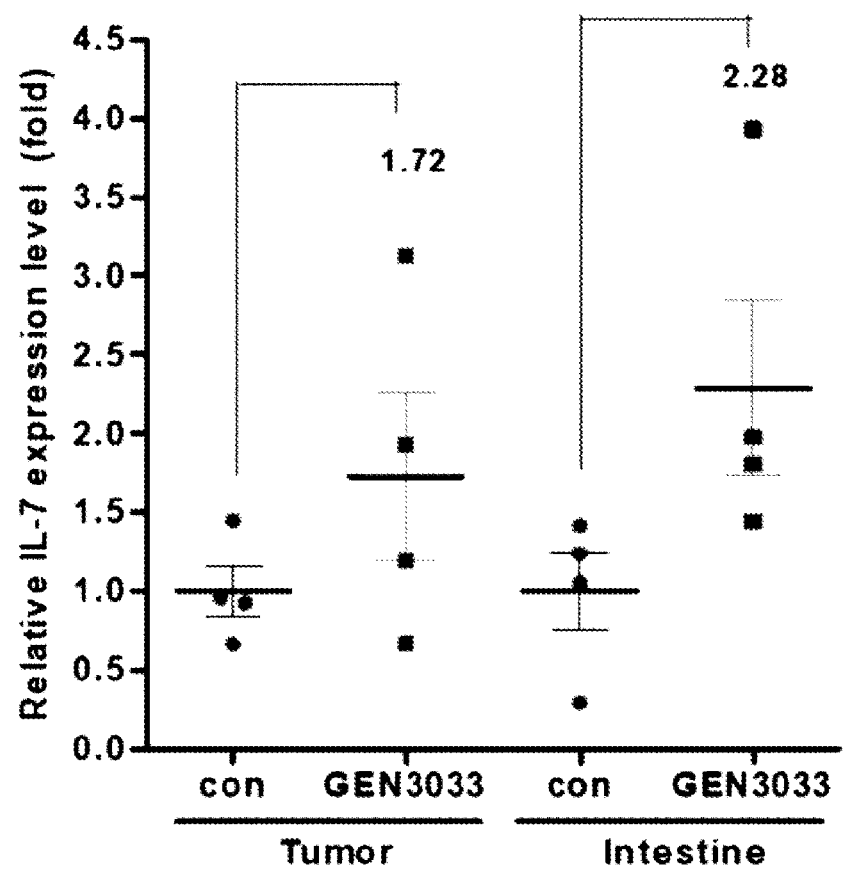
FIG. 17 is a result of measuring the expression of IL-7 in the large intestine and tumor tissue of a mouse tumor model to which the GEN3033 strain was administered.

As shown in FIGS. 16 and 17, it was confirmed that the expression of IL-15 and IL-7 in both tumor and large intestine tissues was increased in the mice of the group administered with GEN3033 compared to the negative control group.

In addition, it was confirmed that the expression of immune factors was higher in the large intestine tissue than in the tumor. This demonstrates that GEN3033 established in the gut activates the immune cells of the large intestine tissue and is involved in the infiltration of immune cells in the tumor microenvironment.

Example 16

Combination Administration of *Lactococcus lactis* GEN3033 Strain and Anticancer Immunotherapeutic Agent In orer to confirm the effect of inhibiting the tumor proliferation when GEN3033 was administered in combination with anti-PD1, an anticancer immunotherapeutic agent, an experiment was performed as follows.

In the tumor model of Example 13, the mice were divided into the group administered with IgG (intraperitoneal administration) and PBS (oral administration) as a negative control group for anti-PD1 and GEN3033, the group administered with GEN3033, the group administered with anti-PD1, the group administered with anti-PD1 in combination with GEN3033, and their efficacy was confirmed, and anti-PD1 (2 mg/kg, BioXCell) was intraperitoneally injected on Day 3, 7, 10, 14, 17, and 21 after cancer induction. The proliferation rate of tumors for each experimental group is shown in FIG. 18.

Figure 18:
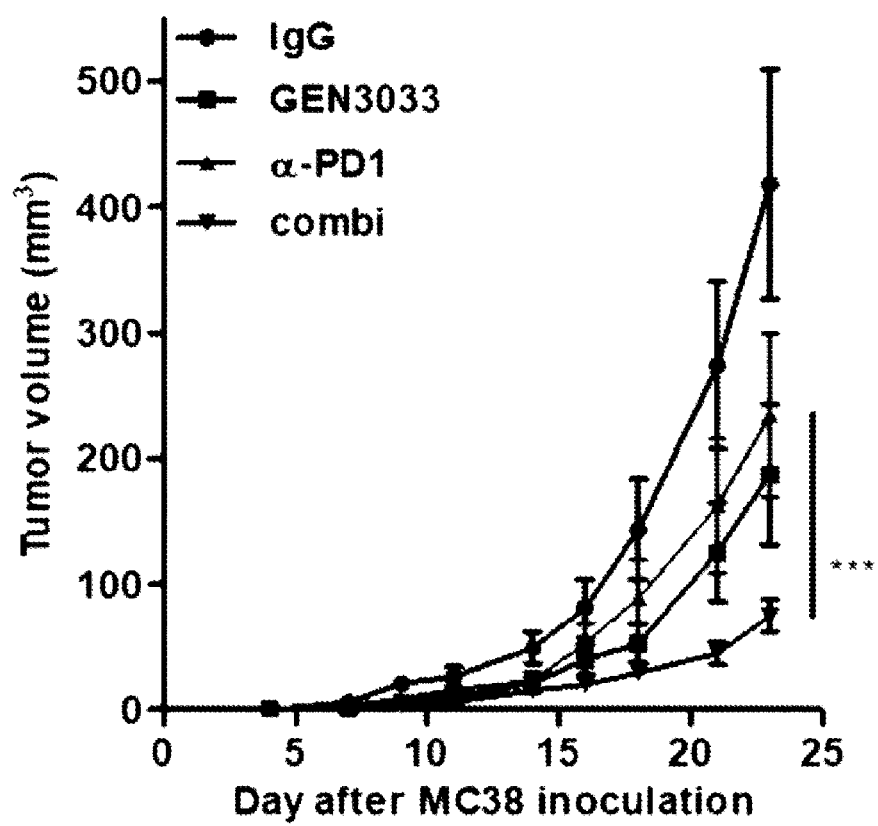
FIG. 18 shows an effect of inhibiting the tumor proliferation when the GEN3033 strain is administered to a mouse colorectal cancer model, when an anticancer immunotherapeutic agent (anti-PD1) is administered, and when these are administered in combination.

As shown in FIG. 18, it was confirmed that the tumor proliferation rate was reduced in the group administered with GEN3033 and the group administered with anti-PD1 compared to the negative control group. In addition, it was confirmed that the tumor proliferation rate of the group administered with anti-PD1 in combination with GEN3033 was further reduced compared to that of the group administered with each alone.

As a result, it can be seen that GEN3033 alone not only inhibits the tumor proliferation, but also exhibits a synergistic effect on inhibiting the tumor proliferation when administered in combination with anti-PD1 compared to when anti-PD1 was administered alone.

Example 17

Metabolite Regulation of *Lactococcus lactis* GEN3033

Lactic acid bacteria help to decompose and absorb food that is decomposed in the digestive organ through the establishment in the gut, thereby supplying nutrients to each organ in the body. Therefore, in order to confirm the change of metabolites by GEN3033, the serum of the mice obtained in the tumor model of Example 15 was analyzed in the following manner.

Figure 19:
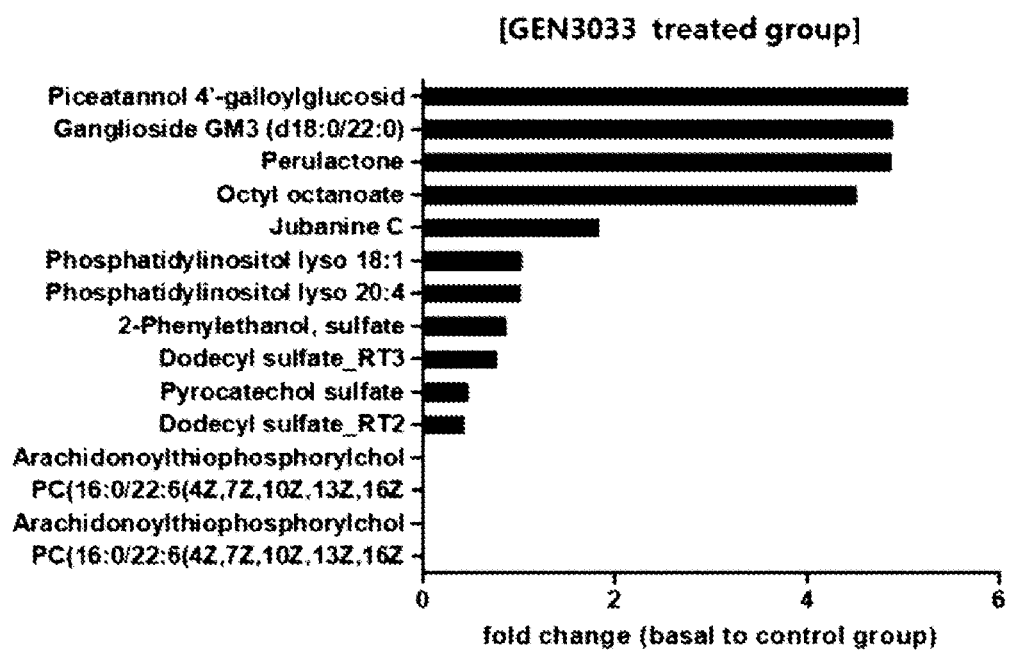
FIGS. 19 to 21 show results of analyzing metabolites in the serum of mice to which the GEN3033 strain and an anticancer immunotherapeutic agent (anti-PD1) are administered alone, or these are administered in combination.
Figure 20:
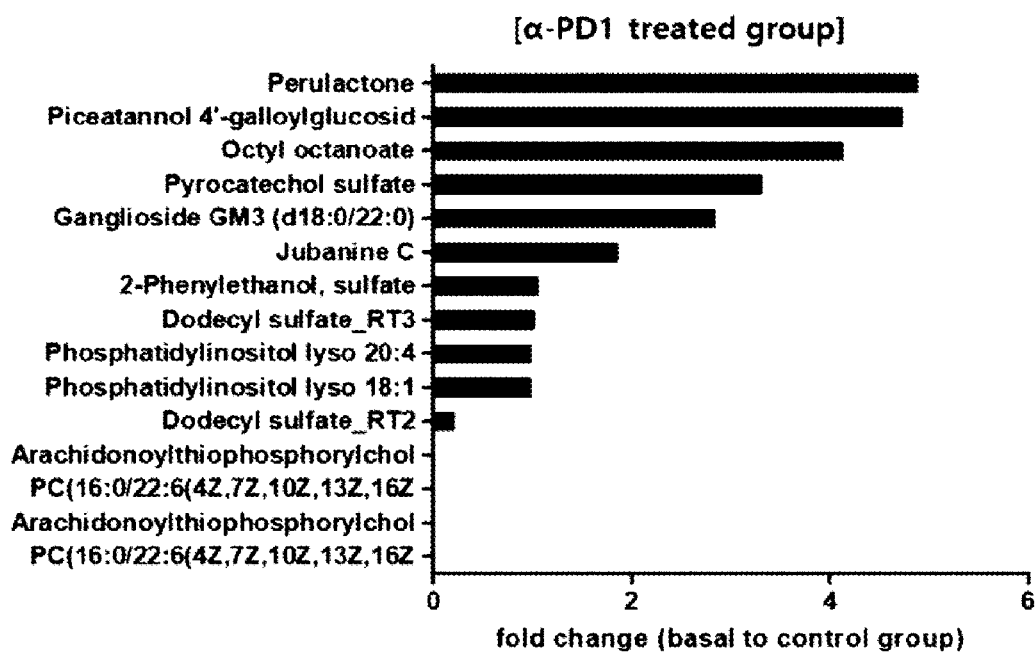
Figure 21:
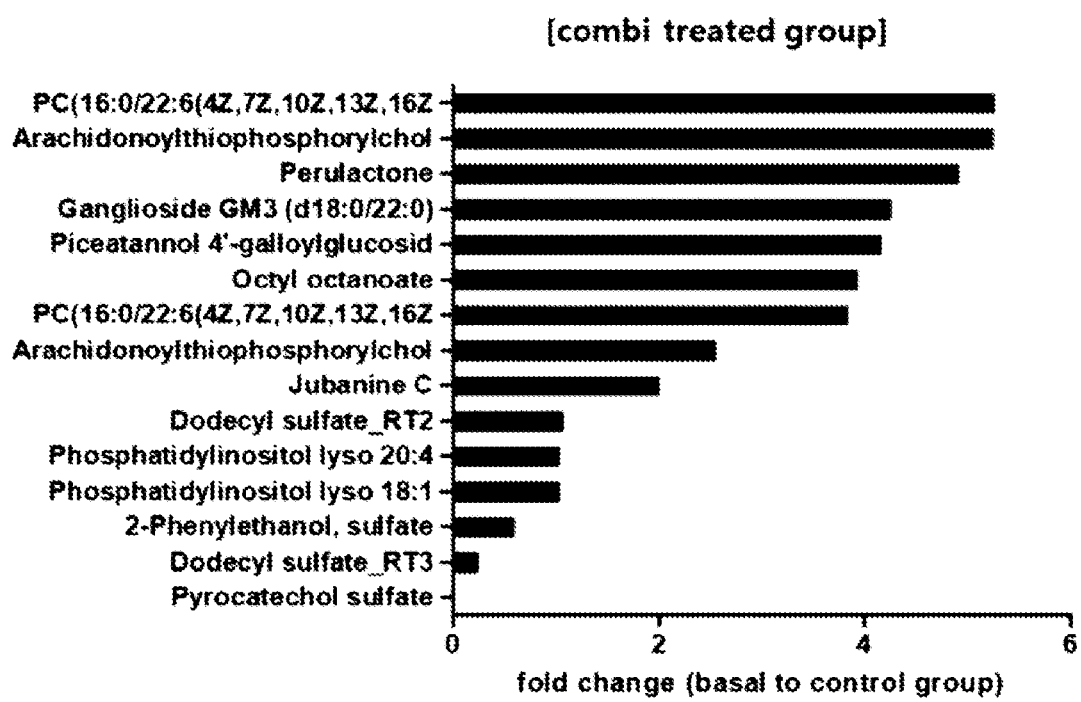

In order to analyze metabolites present in the serum of mice administered with GEN3033, HPLC-MS/MS system (DIONEX UltiMate 3000, Dionex Corporation, Sunnyvale, Calif., USA) composed of Cortex C18+(2.1 mm×100 mm, 2.7 um) columns was used, and Triple TOF 5600+(AB Sciex, USA) was used to detect the material separated from the column. 0.1% formic acid aqueous solution and 0.1% formic acid acetonitrile were used as mobile phases, and all samples were analyzed in Multiple reaction monitoring (MRM) mode, which analyzes two ion transitions, and the results are shown in FIGS. 19 to 21.

As shown in FIG. 19, it was confirmed that the group administered with GEN3033 remarkably increased piceatannol 4'-galloylglucoside, ganglioside GM3, perulactone, octyl octanoate compared to the control group.

As shown in FIG. 20, in the case of the group administered with anti-PD1, perulactone, piceatannol 4'-galloylglucoside, octyl octanoate, pyrocatechol sulfate, ganglioside GM3 were increased compared to the control group.

In addition, as shown in FIG. 21, in the case of the group administered with GEN3033 and anti-PD1 together, perulactone, ganglioside GM3, piceatannol 4'-galloylglucoside, octyl octanoate were equally increased compared to the control group. In addition, compared to the group administered with GEN3033 alone, it was confirmed that arachidonoyl thiophosphorylcholine, PC 16:0/22:6 was increased. In addition, compared to the group administered with anti-PD1 alone, it was confirmed that dodecyl sulfate, arachidonoyl thiophosphorylcholine, PC 16:0/22:6 were increased.

In addition, perulactone, which is a type of steroid, jubanine C, which is mainly used as a food additive, piceatannol 4'-galloylglucoside, and octyl octanoate were measured equally high in the group administered with GEN3033 alone, the group administered with anti-PD1 alone, and the group administered with GEN3033 in combination with anti-PD1 compared to the control group.

In particular, it was confirmed that ganglioside GM3 was further increased in the group administered with GEN3033 alone and the group administered with GEN3033 in combination with anti-PD1 compared to the group administered with anti-PD1 alone.

Phosphatidylinositol (PI)18:1 and 20:4 were further increased in the group administered with GEN3033 alone (1.32 times compared to the control group) and the group administered with GEN3033 in combination with anti-PD1. The PI 20:4 is known to contribute to regulating the immune response by activating macrophages. In addition, it has been reported that the blood content of the three types of phosphatidylinositol, PI18:1, PI20:4, and PI20:2 describe above, is low in patients with cancer compared to normal people. Therefore, the above phosphatidylinositol may be an important biomarker that distinguishes between normal people and patients with cancer. Arachidonoyl thiophosphorylcholine and PC 16:0/22:6 are metabolites belonging to phospholipid, and when stimulation such as an inflammatory response occurs, abnormality in choline metabolism occurs, which cause the damage of cell membrane, thereby leading to a decrease in phospholipid levels. Therefore, the decrease of arachidonoyl thiophosphorylcholine and PC 16:0/22:6 is known as a marker for the damage of cell membrane and inflammatory response.

As shown in FIG. 21, when GEN3033 was administered in combination with anti-PD1, the level of arachidonoyl thiophosphorylcholine and PC 16:0/22:6 was remarkably increase compared to the control group, indicating that the combination administration of GEN3033 and anti-PD1 relieve inflammatory response in the cells.

Through the analysis of such metabolites, it can be seen that changes in metabolites due to intestinal establishment of GEN3033 play an important role in immune response and anticancer efficacy.

Example 18

Effect of *Lactococcus lactis* GEN3033 Strain on Inhibiting the Tumor Proliferation in Anticancer Immunotherapeutic Agent Resistant Lung Cancer Model (In Vivo)

Based on the results in Example 16, it was confirmed that when GEN3033 was administered in combination with anti-PD1, an anticancer immunotherapeutic agent, the effect of inhibiting the tumor proliferation was improved in a colorectal cancer model sensitive to an anticancer immunotherapeutic agent. Based on the above, in order to confirm whether the anticancer efficacy is improved when GEN3033 is administered in combination with anti-PD1 even in a lung cancer model resistant to an anticancer immunotherapeutic agent, the following experiment was performed.

The test was performed in the same manner as in Example 16 on a tumor model into which LLC1 lung cancer was transplanted. The mice were divided into the group administered with IgG (intraperitoneal administration) and PBS (oral administration) as a negative control group for anti-PD1 and GEN3033, the group administered with GEN3033, the group administered with anti-PD1, and the group administered with anti-PD1 in combination with GEN3033, and their efficacy was confirmed. Anti-PD1 (2 mg/kg, BioXCell) was intraperitoneally injected on Day 10, 14, 17, 21, and 23 after cancer induction. The proliferation rate of tumors for each experimental group was measured, and the results are shown in FIG. 22.

Figure 22:
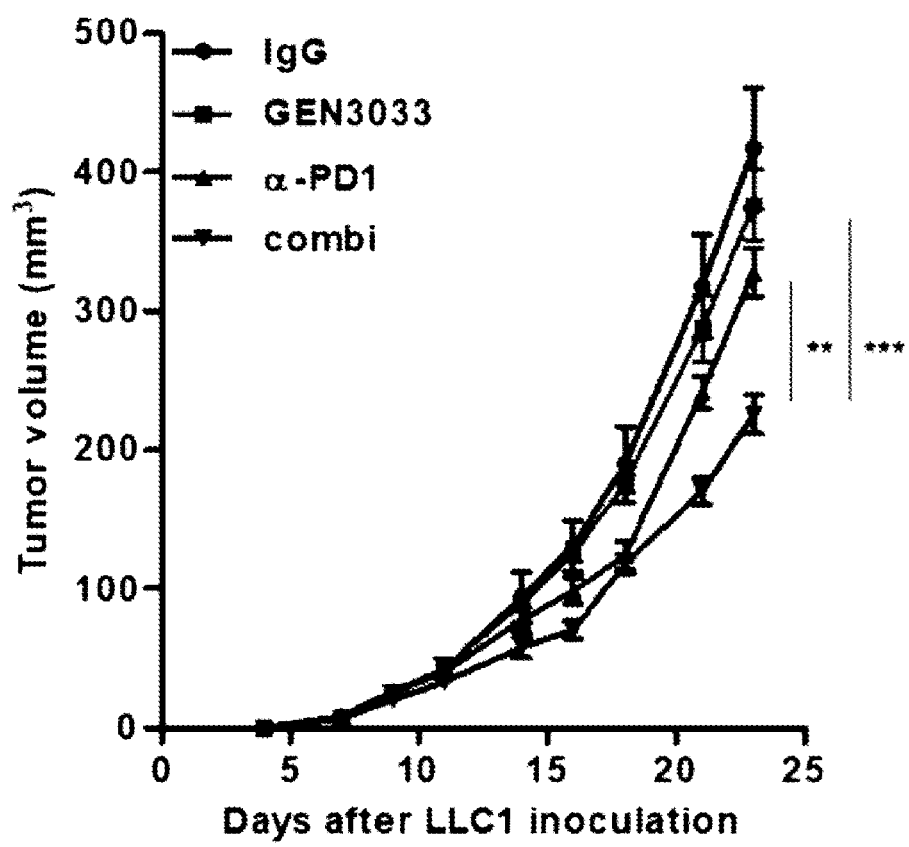
FIG. 22 shows an effect of inhibiting the tumor proliferation according to the combination administration of an anticancer immunotherapeutic agent (anti-PD1) and GEN3033 in a mouse lung cancer model.

As shown in FIG. 22, it was confirmed that the tumor proliferation rate was reduced in the group administered with GEN3033 and the group administered with anti-PD1 compared to the negative control group. In addition, it was confirmed that the tumor proliferation rate of the group administered with anti-PD1 in combination with GEN3033 was further reduced compared to that of the group administered with each alone.

As a result, it can be seen that GEN3033 alone not only inhibits the tumor proliferation, but also exhibits a synergistic effect on inhibiting the tumor proliferation when administered in combination with anti-PD1 compared to when anti-PD1 was administered alone even in a lung cancer model resistant to an anticancer immunotherapeutic agent.

Example 19

Confirmation of Efficacy of Combination Administration of *Lactococcus lactis* GEN3033 and Anticancer Chemotherapeutic Agent or Anticancer Immunotherapeutic Agent In order to further confirm whether GEN3033 remarkably increased the antitumor effect even in combination treatment with an anticancer chemotherapeutic agent or an anticancer immunotherapeutic agent other than anti-PD1, the following experiment was performed.

As an anticancer chemotherapeutic agent, cisplatin, oxaliplatin, 5-FU, cyclophosphamide, and paclitaxel were used, and in the colorectal cancer cell line HCT116, the cell viability was confirmed when each concentration of the anticancer agent and 0.5% concentration of GEN3033 were administered in combination, and the results are shown in FIGS. 23 to 27.

Figure 23:
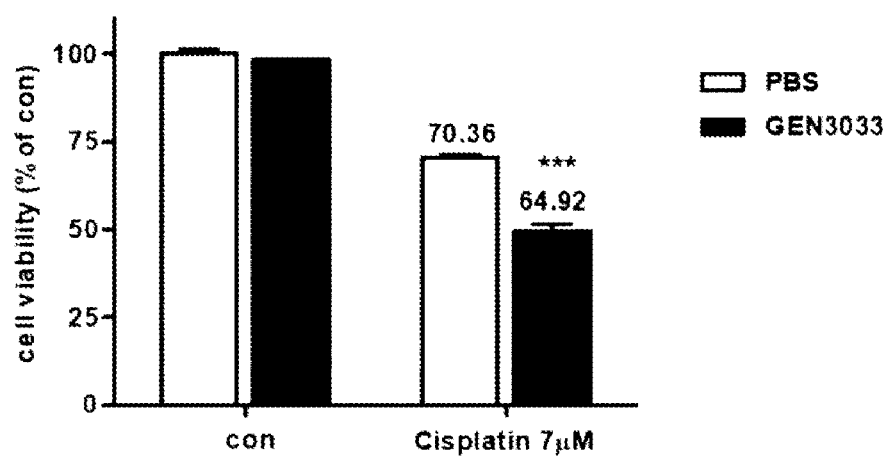
FIGS. 23 to 27 show the efficacy of cancer cell death according to the combination treatment of the GEN3033 strain and an anticancer chemotherapeutic agent (cisplatin, oxaliplatin, 5-FU, cyclophosphamide, paclitaxel) against cancer cell lines.
Figure 24:
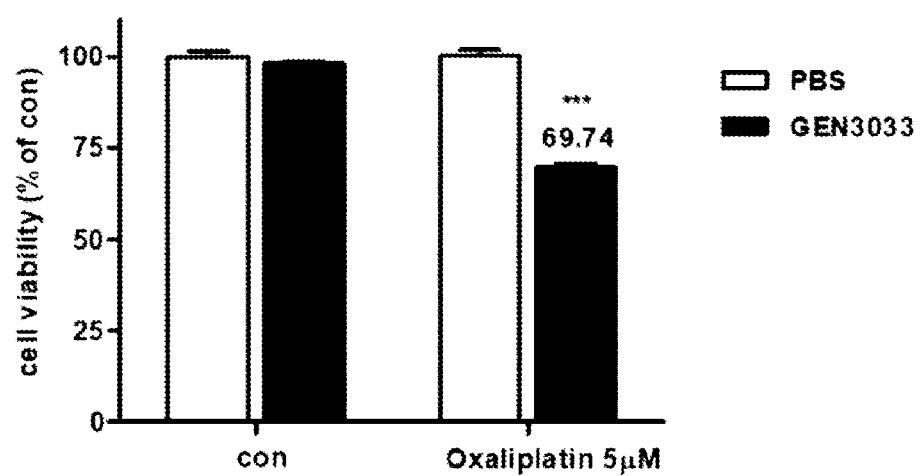
Figure 25:
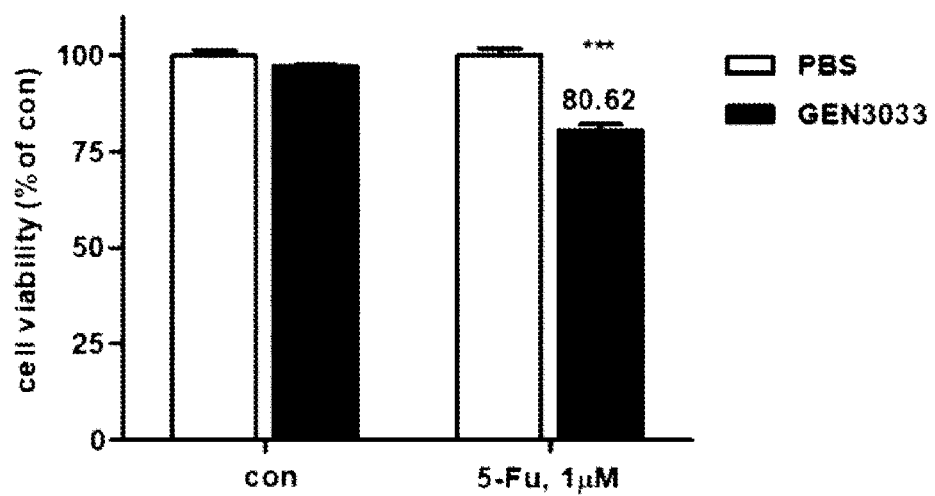
Figure 26:
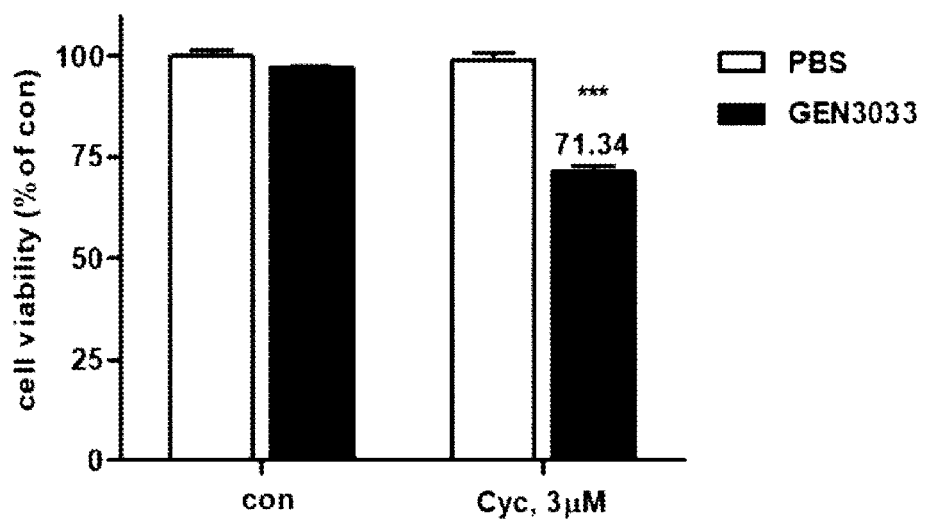
Figure 27:
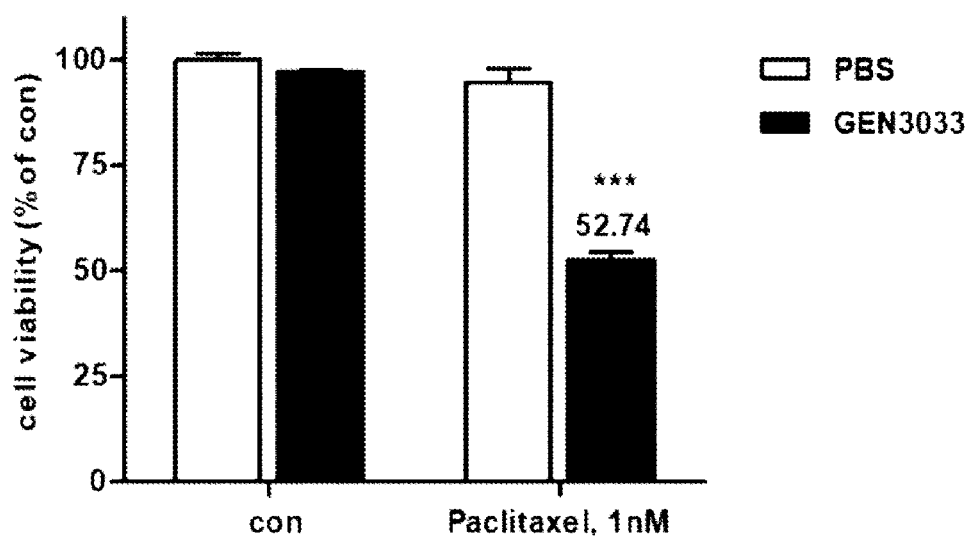

As shown in FIG. 23, it was found that the cell viability was remarkably reduced when treated with GEN3033 in combination with 7 μM Cisplatin compared to when treated with 7 μM Cisplatin alone. In addition, as shown in FIGS. 24 to 27, it was confirmed that the cancer cell death was remarkably high in the case of combination treatment of GEN3033 compared to the case of treatment with oxaliplatin, 5-FU, cyclophosphamide and paclitaxel alone at each concentration showing a cell viability of 90% or more in HCT116.

That is, it was found that GEN3033 had a synergistic anticancer effect by remarkably reducing the viability of the cancer cells when administered in combination with an anticancer chemotherapeutic agent.

In addition, in order to confirm the activity of immune cells and the corresponding decrease in the viability of tumor cells by treating in combination with anti-PDL1, which is another anticancer immunotherapeutic agent, the following experiment was performed. PBMC and T cells were isolated from the spleen and bone marrow of mice, and PBMC induced the differentiation of macrophages through reaction with GEN3033 and then stimulated the activity of T cells. The supernatant of the activated immune cells was separated, put into MC38 tumor cells with anti-PDL1 and reacted for 24 hours, and then the viability of MC38 was confirmed with FACs apparatus. The results are shown in FIG. 28.

Figure 28:
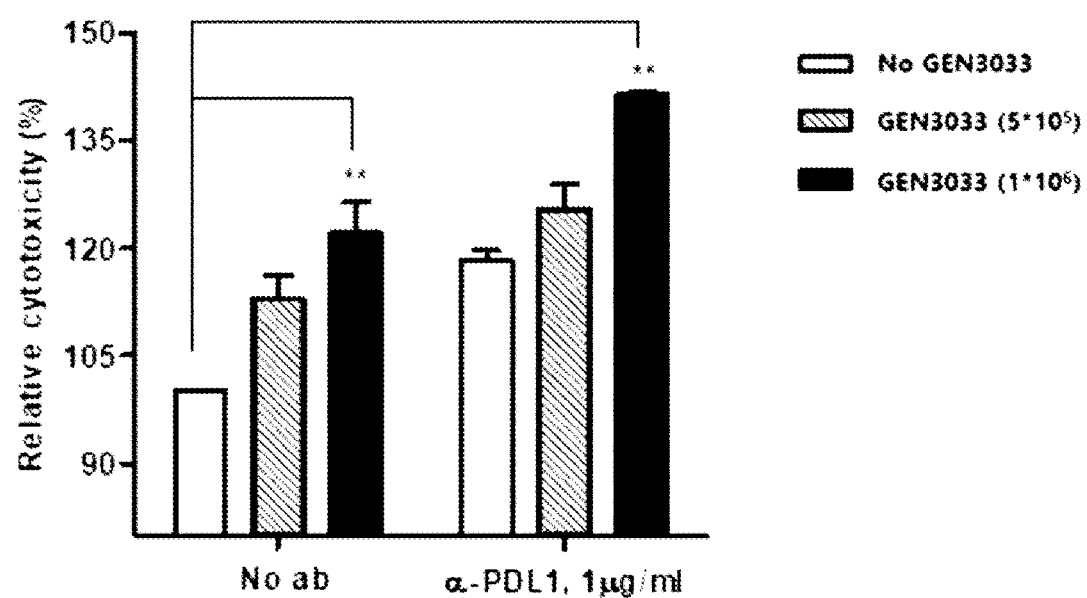
FIG. 28 shows the efficacy of cancer cell death of the GEN3033 strain and an anticancer immunotherapeutic agent (anti-PDL1) using mouse blood and cancer cell lines.

As shown in FIG. 28, it was confirmed that the viability of the cancer cell lines was reduced by 12.82% and 22.02% according to the reaction with GEN3033 even without treatment with an anticancer immunotherapeutic agent. In addition, it was confirmed that the viability of cancer cell lines was reduced by 18.33% by anti-PDL1 (1 mg/mL) alone, whereas the viability of cancer cell lines was reduced by 25.44% and 41.23% when treated with anti-PDL1 (1 mg/mL) in combination with GEN3033. Through the above, it can be confirmed that GEN3033 has an excellent anticancer efficacy even when administered in combination with other anticancer immunotherapeutic agent, such as anti-PDL1, in addition to anti-PD1.

Example 20

Antitumor Enhancing Effect According to Combination Administration of *Lactococcus lactis* GEN3033 Strain and Anticancer Immunotherapeutic Agent (In Vitro Experiment)

PBMCs (peripheral blood mononuclear cells) were collected from the human blood using Ficoll, and then red blood cells were removed through RBC lysis buffer, and the number of living cells was counted, and the cells were cultured for 24 hours in a round bottom 96 well plate containing lactic acid bacteria ($3\times10^5$/50 ul/well) by adding PBMC $3 \times 10^4$ cells/50 μl to each well.

The colon cancer cell line HCT116 was mixed with 5 μM of CFSE (carboxyfluorescein succinimidyl ester) in RPMI medium without FBS, and reacted at 37° C. for 5 minutes, and then RPMI1640 medium containing FBS was added, and stored on ice for 10 minutes. After the supernatant was removed by centrifugation, the obtained cells were mixed with RPMI1640 containing 10% FBS, and then the number of cells was counted, and $3\times10^4$ cells/100 μl were added to each well of the above prepared 96 well plate.

Thereafter, each well to which cancer cells were added was treated with each antibody PD1 (Pembrolizumab, A2005, Selleckem), PD-L1 (Atezolizumab, A2004, Selleckem), CTLA-4 (Ipilimumab, A2001, Selleckem) within the concentration range of 20 to 30 ug/mL, and cultured for 24 hours, and then the cells were stained with 7-aminoactinomycin D (7-AAD; BD Pharmingen, San Diego, CA, USA) to identify the cells lysed in a mixture of PBMC and cancer cell lines. Staining for CFSE and 7-AAD using FACSDiVa software (BD Biosciences) was measured to confirm the cell lysis ability of PBMC against cancer cell lines, and the results are shown in FIG. 29.

Figure 29:
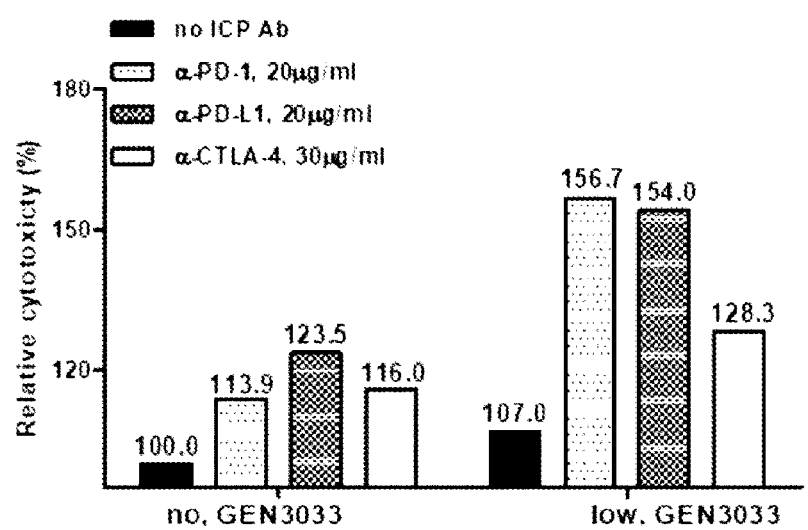
FIG. 29 shows the efficacy of cancer cell death according to the combination treatment of the GEN3033 and an anticancer immunotherapeutic agent (anti-PD1, anti-PD-L1, anti-CTLA4) using human blood and cancer cell lines.

As shown in FIG. 29, it was found that when the cancer cell death (cytotoxicity) caused by PBMC was set to 100%, the cancer cell death (cytotoxicity) caused by GEN0333 alone was 107.0% increase, and the cancer cell death caused by anti-PD1, an anticancer immunotherapeutic agent used in clinical practice, was 113.9%, and the cancer cell death caused by anti-PD-L1 was 123.5%, and the cancer cell death caused by antiCTLA-4 was 116.0%. On the other hand, it was confirmed that when treated with the anticancer immunotherapeutic agent in combination with GEN3033, the cancer cell death caused by anti-PD1 was 156.7%, and the cancer cell death caused by anti-PD-L1 was 154.0%, and the cancer cell death caused by antiCTLA-4 was 128.3%.

As a result, it can be seen that compared to the effect on the cancer cell death when treated alone, the effect on the cancer cell death when treated in combination is remarkably increased.

[Accession Number]

*Bifidobacterium bifidum* MG731

Name of Depositary Authority: Korean Collection for Type Cultures, Korea Research Institute of Bioscience and Biotechnology Accession Number: KCTC13452BP Date of Deposit: Jan. 4, 2018

*Lactococcus lactis* GEN3033

Name of Depositary Authority: Korean Collection for Type Cultures, Korea Research Institute of Bioscience and Biotechnology Accession Number: KCTC13684BP Date of Deposit: Oct. 25, 2018

What is claimed is:

1. A pharmaceutical composition comprising a *Bifidobacterium bifidum* MG731 strain KCTC13452BP and a pharmaceutically acceptable excipient, and further comprising an anticancer chemotherapeutic agent or an anticancer immunotherapeutic agent.

2. The pharmaceutical composition of claim 1, wherein the anticancer chemotherapeutic agent is selected from the group consisting of oxaliplatin, pemetrexed, cisplatin, gemcitabine, carboplatin, fluorouracil (5-FU), cyclophosphamide, paclitaxel, vincristine, etoposide, and doxorubicin.

3. The pharmaceutical composition of claim 1, wherein the anticancer immunotherapeutic agent is selected from the group consisting of anti-PD1, anti-PDL1, anti- CTLA, anti-Tim3, and anti-LAG3.

4. A method for treating cancers, the method comprising administering an effective amount of a *Bifidobacterium bifidum* MG731 strain KCTC13452BP.

5. The method of claim 4, wherein the cancer is selected from the group consisting of lung cancer, colorectal cancer, gastric cancer, breast cancer, and liver cancer.

6. The method of claim 4, wherein the *Bifidobacterium bifidum* MG731 strain exhibits an anticancer effect by decreasing the mobility of cancer cells.

7. The method of claim 4, wherein the *Bifidobacterium bifidum* MG731 strain exhibits an anticancer effect by inhibiting the expression of angiogenic factors.

8. The method of claim 7, wherein the angiogenic factors comprises one or more of the expression of VEGF (vascular endothelial growth factor), Ang1 (Angiopoietin1), or Ang2 (Angiopoietin2).

9. The method of claim 4 further comprises administering an anticancer chemotherapeutic agent or an anticancer immunotherapeutic agent.

10. The method of claim 9, wherein the anticancer chemotherapeutic agent is selected from the group consisting of oxaliplatin, pemetrexed, cisplatin, gemcitabine, carboplatin, fluorouracil (5-FU), cyclophosphamide, paclitaxel, vincristine, etoposide, and doxorubicin.

11. The method of claim 9, wherein the anticancer immunotherapeutic agent is selected from the group consisting of anti-PD1, anti-PDL1, anti-CTLA, anti-Tim3, and anti-LAG3.

12. The method of claim 9, wherein the *Bifidobacterium bifidum* MG731 strain and the anticancer chemotherapeutic agent or the anticancer immunotherapeutic agent are administered simultaneously in one formulation, or are administered simultaneously or sequentially in separate formulations.

13. The method of claim 4, wherein the cancer is selected from the group consisting of melanoma, squamous cell carcinoma, breast cancer, head and neck cancer, thyroid cancer, soft tissue sarcoma, osteosarcoma, testis cancer, prostate cancer, ovarian cancer, bladder cancer, skin cancer, brain cancer, angiosarcoma, mast cell tumor, leukemia, lymphoma, liver cancer, lung cancer, pancreatic cancer, gastric cancer, kidney cancer, colorectal cancer, hematopoietic tumor, neuroblastoma, epidermal carcinoma, or a metastatic cancer thereof.

14. The method of claim 4, wherein the *Bifidobacterium bifidum* MG731 strain exhibits one or more of anticancer, anti-inflammatory, antioxidant, or immune enhancing effects.

15. The method of claim 14, wherein the *Bifidobacterium bifidum* MG731strain inhibits the expression of TNF-α.

16. A food composition comprising a *Bifidobacterium bifidum* MG731 strain KCTC13452BP and a food additive.

17. A method for ameliorating cancers, the method comprising administering an effective amount of a *Bifidobacterium bifidum* MG731 strain KCTC13452BP.

* * * * *